(12) United States Patent
Breton et al.

(10) Patent No.: US 11,901,079 B2
(45) Date of Patent: *Feb. 13, 2024

(54) SYSTEM, METHOD AND COMPUTER READABLE MEDIUM FOR DYNAMICAL TRACKING OF THE RISK FOR HYPOGLYCEMIA IN TYPE 1 AND TYPE 2 DIABETES

(71) Applicant: University of Virginia Patent Foundation, Charlottesville, VA (US)

(72) Inventors: Marc D. Breton, Charlottesville, VA (US); Boris P. Kovatchev, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 43 days.

This patent is subject to a terminal disclaimer.

(21) Appl. No.: 17/683,676

(22) Filed: Mar. 1, 2022

(65) Prior Publication Data
US 2022/0262519 A1 Aug. 18, 2022

Related U.S. Application Data

(63) Continuation of application No. 15/958,257, filed on Apr. 20, 2018, now Pat. No. 11,289,201, which is a (Continued)

(51) Int. Cl.
*G08B 21/04* (2006.01)
*G16H 50/20* (2018.01)
(Continued)

(52) U.S. Cl.
CPC .......... *G16H 50/20* (2018.01); *A61B 5/0017* (2013.01); *A61B 5/0022* (2013.01); (Continued)

(58) Field of Classification Search
USPC .......... 340/539.12, 539.1, 573.1, 691.6, 692, 340/5.52, 5.82, 286.07
See application file for complete search history.

(56) References Cited

U.S. PATENT DOCUMENTS 11,289,201 B2 * 3/2022 Breton ................. A61B 5/0017
2008/0154513 A1 6/2008 Kovatchev et al.
(Continued)

FOREIGN PATENT DOCUMENTS

WO 2015/078975 A1 6/2015

*Primary Examiner* — Daniel Previl
(74) *Attorney, Agent, or Firm* — Potomac Law Group, PLLC; Vincent M DeLuca; Brian H. Buck

(57) ABSTRACT

A system, method and non-transient computer readable medium for tracking hypoglycemia risk in patients with diabetes exercise. A system may include a digital processor configured to execute instructions to receive an input from each available data source of a plurality of intermittently available data sources; determine a plurality of probability signals for impending hypoglycemia, wherein each probability signal is based on one or more of the inputs from the available data sources or a lack of input from an unavailable data source; wherein a probability signal for each unavailable data source is assigned a value corresponding to a zone of uncertainty; and determine an aggregate risk of hypoglycemia based on the plurality of intermittently data sources by aggregating the plurality of probability signals.

19 Claims, 9 Drawing Sheets

Related U.S. Application Data continuation of application No. PCT/US2016/058234, filed on Oct. 21, 2016.

(60) Provisional application No. 62/244,496, filed on Oct. 21, 2015.

(51) Int. Cl.

| | |
|---|---|
| *A61B 5/145* | (2006.01) |
| *A61B 5/00* | (2006.01) |
| *G16H 50/30* | (2018.01) |
| *G06N 7/01* | (2023.01) |
| *A61B 5/11* | (2006.01) |
| *A61M 5/172* | (2006.01) |

(52) U.S. Cl.
CPC ............ *A61B 5/1118* (2013.01); *A61B 5/145* (2013.01); *A61B 5/14532* (2013.01); *A61B 5/7275* (2013.01); *A61B 5/746* (2013.01); *A61M 5/1723* (2013.01); *G06N 7/01* (2023.01); *G16H 50/30* (2018.01); *A61M 2205/3569* (2013.01); *A61M 2205/3592* (2013.01); *A61M 2205/50* (2013.01); *A61M 2230/201* (2013.01)

(56) References Cited

U.S. PATENT DOCUMENTS

| | | | |
|---|---|---|---|
| 2009/0281839 A1* | 11/2009 | Lynn | G16H 10/60 |
| | | | 382/128 |
| 2011/0077494 A1 | 3/2011 | Doniger et al. | |
| 2013/0079613 A1* | 3/2013 | Kovatchev | A61B 5/7225 |
| | | | 600/365 |
| 2013/0109944 A1 | 5/2013 | Sparacino et al. | |
| 2013/0274580 A1* | 10/2013 | Madsen | A61B 5/7264 |
| | | | 600/365 |
| 2013/0311102 A1 | 11/2013 | Minor | |
| 2013/0321425 A1 | 12/2013 | Greene et al. | |
| 2014/0200559 A1 | 7/2014 | Doyle, III et al. | |
| 2015/0018633 A1* | 1/2015 | Kovachev | A61B 5/486 |
| | | | 600/301 |
| 2015/0073754 A1 | 3/2015 | Okkonen et al. | |
| 2015/0095042 A1* | 4/2015 | Aykroyd | G16H 40/67 |
| | | | 705/2 |

* cited by examiner

SYSTEM, METHOD AND COMPUTER READABLE MEDIUM FOR DYNAMICAL TRACKING OF THE RISK FOR HYPOGLYCEMIA IN TYPE 1 AND TYPE 2 DIABETES

CROSS REFERENCE TO RELATED APPLICATION

This application is a continuation under 35 U.S.C. 120 of copending application Ser. No. 15/958,257 filed Apr. 20, 2018, which is a continuation of prior international application No. PCT/US2016/058234 filed Oct. 21, 2016, which claims priority to U.S. Provisional Patent Application No. 62/244,496, filed on Oct. 21, 2015, the disclosures of which are incorporated herein by reference in their entirety.

BACKGROUND AND SUMMARY

People with diabetes face a life-long optimization problem: to maintain strict glycemic control, as reflected by hemoglobin A1c (HbA1c), without increasing their risk for hypoglycemia. While target HbA1c values of 7% or less result in decreased risk of micro- and macrovascular complications, the risk for severe hypoglycemia increases with tightening glycemic control. Consequently, hypoglycemia has been implicated as the primary barrier to optimal glycemic control. Thus, a strategy for achieving optimal diabetes control can only be successful if both tracking of HbA1c and tracking of the risk for hypoglycemia are available.

HbA1c: In the early 1990's the landmark Diabetes Control and Complications Trial [DCCT, 1, 2, 3] and the Stockholm Diabetes Intervention study [4] clearly indicated that intensive insulin treatment can reduce the long-term complications of type 1 diabetes. In 1998 the UK Prospective Diabetes Study Group established that intensive treatment with insulin or with oral medications to maintain nearly normal levels of glycemia markedly reduces chronic complications in type 2 diabetes as well [5]. HbA1c was identified as the primary marker of long-term average glucose control [6,7] and still remains the gold-standard assay reflecting average glycemia widely accepted in research as a primary outcome for virtually all studies of diabetes treatment, and in the clinical practice as primary feedback to the patient and the physician and a base for treatment optimization.

Hypoglycemia is common in T1DM [8] and becomes more prevalent in T2DM with treatment intensification [9]. However, the DCCT also showed that intensive treatment of diabetes can also increase the risk for severe hypoglycemia (low blood glucose that could result in stupor, unconsciousness, and even death) [8]. Indeed, HbA1c has repeatedly been proven to be an ineffective assessment of patients' risk for hypoglycemia. The DCCT concluded that only about 8% of severe hypoglycemic episodes could be predicted from known variables, including HbA1c [8]; later this prediction was improved to 18% by a structural equation model using history of severe hypoglycemia, awareness, and autonomic symptom score [10]. In subsequent studies, HbA1c has never been significantly associated with severe hypoglycemia [11, 12, 13, 14]. Nevertheless, the physiological mechanisms of hypoglycemia were well established by a number of studies that have investigated the relationships between intensive therapy, hypoglycemia unawareness, and impaired counterregulation [15, 16, 17, 18] and concluded that recurrent hypoglycemia spirals into a "vicious cycle" known as hypoglycemia-associated autonomic failure (HAAF, [19]) observed primarily in type 1, but also in type 2 diabetes [20]. The acute risk for hypoglycemia was attributed to impairments in the systemic reaction to falling BG levels: in health, falling BG concentration triggers a sequence of responses, beginning with attenuation of endogenous insulin production, followed by increase in glucagon and epinephrine and, if BG concentration falls further, resulting in autonomic symptoms and/or neuroglycopenia; in type 1 diabetes, and to some extent in type 2 diabetes, these defense mechanisms are impaired [21, 22, 23]. As a result, hypoglycemia was identified as the primary barrier to optimal diabetes control [24,25]. The clinical optimization problem of diabetes was therefore clearly formulated: reduce average glycemia and exposure to high blood glucose levels (thereby HbA1c), while preventing hypoglycemia.

Self-Monitoring of Blood Glucose (SMBG): Home BG meters offer convenient means for frequent BG determinations through. Most devices are capable of storing BG readings (typically over 150 readings) and have interfaces to download these readings into a computer. The meters are usually accompanied by software that has capabilities for basic data analyses (e.g. calculation of mean BG, estimates of the average BG over the previous two weeks, percentages in target, hypoglycemic and hyperglycemic zones, etc.), log of the data, and graphical representation (e.g. histograms, pie charts) [26, 27, 28, 29]. Analytical methods based on SMBG data are discussed in the next section.

Tracking estimated HbA1c (eA1c): The present inventors published a new approach to real-time dynamical estimation of HbA1c from infrequent self-monitoring (SMBG) data [30]. This method was designed to track changes in average glycemia and was based on a conceptually new approach to the retrieval of SMBG using a mathematical model to estimate HbA1c as the measurable aggregated effect of the action of an underlying dynamical system which translates ambient BG levels into HbA1c values through hemoglobin glycation [30]. A key feature of this approach, among others, is that it is capable of working with infrequent SMBG data typical for type 2 diabetes, e.g. fasting readings on most days and occasional (monthly) 7-point SMBG profiles. Thus, the eA1c algorithm differed from all previously introduced techniques by its use of an underlying model that "filled in" the gaps between sparse SMBG values, thereby allowing continuous tracing of average glycemia. The present inventors adopted this model-based approach because, while it is generally true that HbA1c is roughly proportional to the average BG of a person over the past 2-3 months and a number of linear and nonlinear formulas have been used to describe this relationship [31-40], it is also established that average BG estimated from HbA1c using a linear formula and average BG estimated from SMBG are discordant measures of glycemic control [41]. The discrepancies have been quantified by the hemoglobin glycation index (HGI, equal to observed HbA1c—predicted HbA1c), where the prediction is a linear regression formula based on average BG derived from 7-point daily profiles collected quarterly [42], or on average fasting BG [43].

Risk Analysis of BG Data [44]: The computation of mean glucose values from SMBG data is typically used as a descriptor of overall glycemic control. Computing pre- and post-meal averages and their difference can serve as an indication of the effectiveness of pre-meal bolus timing and amount. Similarly, the percentages of SMBG readings within, below, or above preset target limits would serve as indication of the general behavior of BG fluctuations. The suggested limits are 70 and 180 mg/dl (3.9-10 mmol/l), which create three suggested by the DCCT and commonly accepted bands: hypoglycemia (BG<=70 mg/dl); normoglycemia (70 mg/dl<BG<=180 mg/dl) and hyperglycemia (BG>180 mg/dl) [1]. In a series of studies the present inventors have shown that specific risk analysis of SMBG data could also capture long-term trends towards increased risk for hypoglycemia [11, 12, 13], and could identify 24-hour periods of increased risk for hypoglycemia [14,45]. The sequential steps of the Risk Analysis are:

Symmetrization of the BG scale: A nonlinear transformation is applied to the BG measurements scale to map the entire BG range (20 to 600 mg/dl, or 1.1 to 33.3 mmol/l) to a symmetric interval. This is needed because the distribution of BG values of a person with diabetes is asymmetric, typically skewed towards hyperglycemia. The BG value of 112.5 mg/dl (6.25 mmol/l) is mapped to zero, corresponding to zero risk for hypo- or hyperglycemia (the present inventors should note that this is not a normoglycemic or fasting value, which in health would be <100 mg/dl; it is zero-risk value pertinent to diabetes). The analytical form of this transformation is $f(BG)=\gamma \cdot [\ln(BG)^{\alpha}-\beta]$, where the parameters are estimated as $\alpha=1.084$, $\beta=5.381$, and $\gamma=1.509$, if BG is measured in mg/dl and $\alpha=1.026$, $\beta=1.861$, and $\gamma=1.794$, if BG is in mmol/l [46].

Computing measures of risk for hypoglycemia and hyperglycemia: A quadratic risk function is defined as by the formula $r(BG)=10 \cdot f(BG)^2$. The function r(BG) ranges from 0 to 100. Its minimum value is achieved at BG=112.5 mg/dl, a safe euglycemic BG reading, while its maximum is reached at the extreme ends of the BG scale. Thus, r(BG) can be interpreted as a measure of the risk associated with a certain BG level. The left branch of this parabola identifies the risk of hypoglycemia, while the right branch identifies the risk of hyperglycemia. Now, let $x_1, x_2, \ldots x_n$ be a series of n BG readings, and let $rl(BG)=r(BG)$ if $f(BG)<0$ and 0 otherwise; $rh(BG)=r(BG)$ if $f(BG)>0$ and 0 otherwise. Then the Low and High Blood Glucose Indices are computed as follows:

$$LBGI = \frac{1}{n}\sum_{i=1}^{n} rl(x_i)^2 \quad HBGI = \frac{1}{n}\sum_{i=1}^{n} rh(x_i)^2$$

Thus, the LBGI is a non-negative quantity that increases when the number and/or extent of low BG readings increases and the HBGI is non-negative quantity that increases when the number and/or extent of high BG readings increases.

Chronic and Acute Risk for hypoglycemia: For the purposes of this disclosure the present inventors will refer to two types of risk factors for hypoglycemia—chronic, reflecting elevated long-term risk for, and acute, reflecting abrupt changes in metabolic status, which increase the risk for immediate hypoglycemia.

Chronic risk factors for hypoglycemia, including low $HbA_{1c}$, history of severe hypoglycemia (SH), unawareness, and intensive therapy, were studied by the DCCT [8] and others [20]. Perhaps the most important messages of these studies are: (i) a major [categorical rather than ordinal] predictor of future SH was the history of SH, and (ii) $HbA_{1c}$ has a modest contribution to the prediction of SH (only 8% in the DCCT,8]. In contrast, variability-based measures accounted for 40-50% of the chronic risk for significant hypoglycemia [12]. As a result, the 2005 American Diabetes Association consensus statement on hypoglycemia concluded that ". . . history of severe hypoglycemia and lower $HbA_{1c}$ levels have limited ability to predict additional episodes. . . [while]>50% of hypoglycemia can be predicted based on risk analysis of self-monitored plasma glucose data over time" [47]. Thus, it has been demonstrated that patterns of chronically elevated (over weeks) risk for hypoglycemia is detectable from SMBG data [13].

Acute risk for hypoglycemia: In health, falling BG concentration triggers a sequence of responses, beginning with attenuation of endogenous insulin production, and followed by increase in glucagon and epinephrine [21]. In T1DM endogenous insulin secretion is practically non-existent, thus the first defense mechanism against hypoglycemia is unavailable. Further, it has been shown that glucagon response is impaired [48), and epinephrine response is typically attenuated [15]. Antecedent hypoglycemia has been shown to shift to lower BG the thresholds for autonomic, symptomatic, and cognitive responses to subsequent hypoglycemia, thereby impairing glycemic defenses and reducing detection of hypoglycemia [49]. These effects are summarized by the concept of HAAF [19]. Thus, HAAF is a result of hormonal deficiency and behavioral triggers, elevating risks for hypoglycemia on the time frame of a few days. Specific 48-hour SMBG patterns of acutely increased risk for hypoglycemia have been associated with SH and recurrent hypoglycemic episodes [45].

Multi-Source Estimation of the Risk for Hypoglycemia: U.S. Pat. No. 6,923,763 B1 issued on Aug. 2, 2005 [50] pointed to the possibility of using multiple data sources relevant to the various factors determining the chronic and acute risks for hypoglycemia to determine a compound risk for hypoglycemia. This technology was based on, among other things, a mathematical model using SMBG data as well as information about prior insulin delivery, information about exercise based on heart rate signal, and information about autonomic system activation based on heart rate variability. The system, method, and computer readable medium proposed here is unique in its concept and mathematical methods due to, but not limited thereto, the following: the present inventors now combine multi-source data that using a stochastic probability aggregation procedure which allows these various data sources to be available or not available to the overall risk estimation; in contrast, for example, the present inventors' previous technology relied on a single deterministic model requiring all inputs from all data sources to be available simultaneously.

Presently disclosed is a method for tracking hypoglycemia risk that includes obtaining an input from each available data source of a plurality of intermittently available data sources; determining a plurality of probability signals for impending hypoglycemia, wherein each probability signal is based on one or more of the inputs from the available data sources or a lack of input from an unavailable data source; wherein a probability signal for each unavailable data source is assigned a value corresponding to a zone of uncertainty; and determining an aggregate risk of hypoglycemia based on the plurality of intermittently data sources by aggregating the plurality of probability signals. In some embodiments, one data source of the plurality of intermittently available data sources comprises self-monitoring blood glucose (SMBG) data. In some embodiments, determining the plurality of probability signals for impending hypoglycemia includes determining a chronic risk and/or an acute risk of hypoglycemia based on the SMBG data. In some embodiments, obtaining the self-monitoring blood glucose (SMBG) data comprises receiving a blood glucose signal from a continuous blood glucose monitor. In some embodiments, the plurality of intermittently available data sources includes one or more of: a physical activity indication, an insulin delivery indication, a carbohydrate indication, and a non-insulin medicine indication. In some embodiments, the physical activity indication comprises a signal from at least one sensor configured to detect when the user begins to exercise. In some embodiments, one or more of the plurality of intermittently available data sources are automatically monitored and reported. In some embodiments, one or more of the plurality of intermittently available data sources are self-reported by a user. In some embodiments, determining a plurality of probability signals for impending hypoglycemia comprises translating each input from the available data sources into the probability signal for impending hypoglycemia, In some embodiments, the probability signal for impending hypoglycemia is standardized on a scale where minimal risk of hypoglycemia is mapped to zero, maximal risk of hypoglycemia is mapped to 1, a cutoff value differentiating no-risk and elevated risk is mapped to 0.5, and the zone of certainty in determining risk of hypoglycemia is mapped to 0.5. In some embodiments, the method further includes using the aggregate risk of hypoglycemia to estimate the probability of a hypoglycemic event. In some embodiments, aggregating the plurality of probability signals includes combining the plurality of probability signals using the Bayes formula. In some embodiments, the method further includes displaying an alert on a display of a portable computing device based on the determined aggregated risk of hypoglycemia. In some embodiments, the method further includes communicating an instruction to an insulin pump based on the determined aggregated risk of hypoglycemia.

Also disclosed is a system for tracking hypoglycemia risk that includes a digital processor; and a memory in communication with the digital process, wherein the memory contains instructions configured to be executed by the processor to receive an input from each available data source of a plurality of intermittently available data sources; determine a plurality of probability signals for impending hypoglycemia, wherein each probability signal is based on one or more of the inputs from the available data sources or a lack of input from an unavailable data source; wherein a probability signal for each unavailable data source is assigned a value corresponding to a zone of uncertainty; and determine an aggregate risk of hypoglycemia based on the plurality of intermittently data sources by aggregating the plurality of probability signals. In some embodiments, the system further includes a display; and wherein the digital processor is configured to generate an alert on the display if the determined aggregate risk of hypoglycemia indicates a probability of a hypoglycemic event exceeds a predetermined threshold. In some embodiments, the system further includes a continuous blood glucose monitoring sensor in communication with the digital processor, the continuous blood glucose monitoring sensor configured to generate self-monitored blood glucose data and communicate said data to the digital processor. In some embodiments, the system further includes an insulin pump in communication with the digital processor and configured to dispense or not dispense insulin in response the determined aggregate risk of hypoglycemia.

BRIEF DESCRIPTION OF THE DRAWINGS

Reference is made to the accompanying drawings in which particular embodiments are illustrated as described in more detail in the description below.

DETAILED DESCRIPTION OF THE DRAWINGS

Figure 1A:
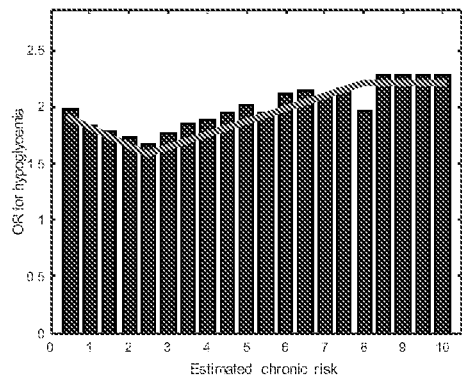
FIGS. 1A and 1B are exemplary graphs of odds ratio and standardization function for hypoglycemia based on chronic risk.

An aspect of an embodiment of the present invention provides, but is not limited thereto, a system, method, and computer readable medium for dynamical tracking of the risk for hypoglycemia in type 1 and type 2 diabetes using multiple information sources.

Data Sources: The method (and system and computer readable medium) for dynamical tracking of the risk for hypoglycemia estimates the probability of an upcoming hypoglycemic event (BG below 70 mg/dL) using data from multiple potentially available sources that may include:
(1) Self-monitoring (SMBG) data transformed into BG risk values as described above are used to determine:
 a. Chronic risk for hypoglycemia (developing over weeks), which in type 2 diabetes is typically the risk for hypoglycemia associated with fasting (morning) BG over this period of time, and in type 1 diabetes can be at any time during the day;
 b. Acute risk for hypoglycemia (developing over a few days), which in type 2 diabetes is typically the risk for hypoglycemia associated with fasting (morning) BG over this period of time, and in type 1 diabetes can be at any time during the day;
(2) Information about recent physical activity, which can be:
 a. A self-report using a certain estimation scale, e.g. less-usual-more physical activity or a 0-6 rating of physical activity relative to the patient's baseline, or
 b. Derived from other data sources such as monitoring of heart rate, accelerometer, or other motion signals.
(3) Information about recent insulin delivery, which can be:
 a. A self-report using a certain estimation scale, e.g. less-usual-more insulin or a 0-6 rating of recent insulin amount relative to the patient's baseline, or
 b. Derived from automated data sources such as insulin pump or insulin pen reports;

(4) Information about recent carbohydrate intake, which can be:
   a. A self-report using a certain estimation scale, e.g. less-usual-more food or a 0-6 rating of the amount of recently ingested carbohydrates, or
   b. Derived from automated data sources such as carb logs, or image recognition of foods;
(5) Information about other medications that could trigger hypoglycemia, such a sulfonylurea, GLP-1 agonists, or glucagon suppressors, which can be:
   a. Self-reported, or
   b. Derived from automated data sources such as drug injection pens.

The present inventors should emphasize that not all data sources need to be available simultaneously—any combination of the above data sources, or any other available data sources can be used, as long as the data is processed using the following data standardization procedure:

Data Standardization Procedure: The present inventors translate the output of each data source into probability for impending hypoglycemia. The idea is that at each data source could potentially provide an assessment of the risk for hypoglycemia (e.g. more exercise, less food, or higher acute risk that results from transient autonomic failure), which can be converted into probability for impending hypoglycemia by defining a function that maps the aggregated results from any data source into probability space as follows:
   (i) The least (minimal) risk indicated by the data source is mapped to 0;
   (ii) The most (maximal) risk indicated by the data source is mapped to 1;
   (iii) The cutoff value differentiating no-risk vs. elevated risk for hypoglycemia suggested by the data source is mapped to 0.5;
   (iv) If the data suggest a zone of uncertainty indicating neither lower nor elevated risk for hypoglycemia, the entire zone of uncertainty is mapped to probability to 0.5.

Data standardization is performed for all available data sources at every step of the dynamical tracking procedure. Note that different data sources may be available at different times of the dynamical tracking process. If a data source is temporarily or permanently unavailable, the entire range of this data source is treated as uncertainly zone, meaning that the procedure computing the probability for impending hypoglycemia still passes through this predefined data source, but its output does not change as a result. This is done in order to accommodate temporarily missing data or available data that fall into an uncertainty zone using the same computational sequence. This procedure is detailed below.

Available DATA: SMBG and Behavioral Records were available from NIH studies of behavioral interventions targeting patient education about hypoglycemia that were conducted between 1996 and 2009. All study participants had the diagnosis of type1 diabetes. As reported in the literature, the behavioral records were collected on handheld computers asking several questions about recent patient behavior, including a subjective estimate of most recent Physical Activity [51, 52, 53, 54].

Study 1: 97 subjects; 12985 SMBG readings; 6705 behavioral records
Study 2: 89 subjects; 15230 SMBG reading; 6209 behavioral records
Study 3: 120 subjects; 188390 SMBG readings; 28224 behavioral records The data from Studies 1 and 2 were used as a training data set to develop the models described below and to estimate all model parameters. Then, to validate the procedure, all models and all model parameters were fixed and the resulting procedure was applied without any further changes to the data from Study 3. This two-step approach ensures the applicability of the procedure to data sets that are independent from the data used for its development.

Dynamical tracking of SMBG-based Risk: The following first-order dynamical model is used to track the risk of hypoglycemia associated with SMBG readings, typically fasting BGs:

$$\frac{\partial \overline{Risk}}{\partial t} = -\frac{1}{\tau_{Risk}}(\overline{Risk} - f(SMBG_t))$$

where the driving function of the model $f$ ($SMBG_t$) is obtained by computing the Low Blood Glucose Index (LBGI) on daily fasting BG (SMBG collected between 6 AM and 10 AM) over several days. The duration of this time period depends on whether Chronic or Acute risk is assessed and can range from several weeks for Chronic Risk to a few days for Acute risk. The time constant of the model $\tau_{Risk}$ is a model-specific parameter which characterizes chronic vs. acute risk estimation as described below:

Tracking the Chronic SMBG Risk for Hypoglycemia: For chronic risk component estimation:
   the driving function fChronic($SMBG_t$) equals the LBGI computed from fasting (morning) SMBG values collected during the past week;
   the time constant of the dynamical model is fixed at $\tau$ChronicRisk=2 weeks.

The iterative procedure providing weekly estimates of the chronic risk runs as follows:

$$eChronicRisk(t_0) = f_{Chronic}(SMBG_{t_0})$$
$$eChronicRisk(t) = 0.6065 \cdot eChronicRisk(t-1) + 0.3935 \cdot f_{Chronic}(SMBG_t)$$

The resulting weekly weights of the LBGI entering this calculation over 5 weeks are then as follows:

| WEEK-5 | WEEK-4 | WEEK-3 | WEEK-2 | WEEK-1 |
|---|---|---|---|---|
| 0 | $w(t_0) = (1-e^{1/\tau}) \cdot e^{-3/\tau}$ | $w(t_1) = (1-e^{1/\tau}) \cdot e^{-2/\tau}$ | $w(t_2) = (1-e^{1/\tau}) \cdot e^{-1/\tau}$ | $w(t_3) = (1-e^{1/\tau})$ |

The chronic risk may also be assessed more of less frequently than weekly, by applying a simple discretization step to the dynamic equation above. A daily chronic risk assessment, which would synchronize with the daily acute risk assessment, would be computed as:

$$eChronicRisk(t_0) = f_{Chronic}(SMBG_{t_0})$$
$$eChronicRisk(t) = 0.9311 \cdot eChronicRisk(t-1) + 0.06894 \cdot f_{Chronic}(SMBG_t)$$

Tracking the Acute SMBG Risk for Hypoglycemia: For the acute risk component estimation:
   the driving function fAcute($SMBG_t$) equals the LBGI computed from fasting (morning) SMBG values collected on the day of assessment;

the time constant of the dynamical model is fixed at TAcuteRisk=3 days.

The iterative procedure providing daily estimates of the chronic risk runs as follows:

$$eAcuteRisk(t_0) = 0.2835 \cdot f_{Acute}(SMBG_{t_0})$$

$$eAcuteRisk(t) = 0.7165 \cdot eAcuteRisk(t-1) + 0.2835 \cdot f_{Acute}(SMBG_t)$$

Acute risk estimates may not be available every day—missing SMBG readings are handled by the data probability aggregation procedure described below.

Figure 1B:
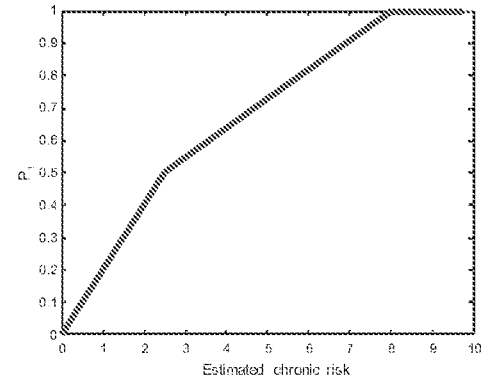

Standardization of the Chronic SMBG Risk for Hypoglycemia: The odds ratios for upcoming hypoglycemia based on the chronic risk alone were used as a guideline to design the chronic risk data standardization function as presented in FIGS. 1A and 2B. The points where the odds ratio changes its slope (FIG. 1A) are natural cut points for a piecewise linear approximation of a standardization function (FIG. 1B).

Figure 2A:
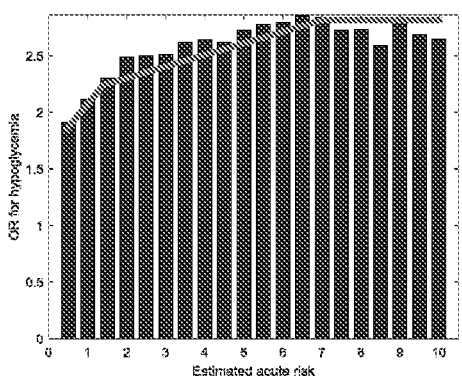
FIGS. 2A and 2B are exemplary graphs of odds ratio and standardization function for hyperglycemia based on acute risk.
Figure 2B:
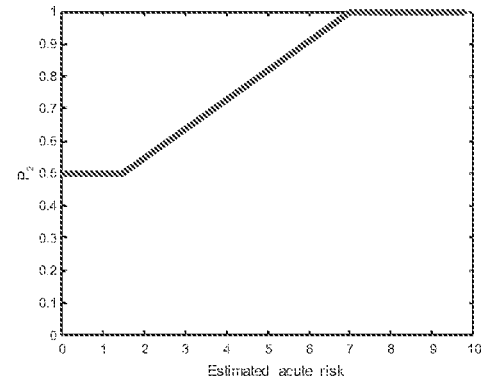

Standardization of the Acute SMBG Risk for Hypoglycemia: The odds ratios for upcoming hypoglycemia based on the acute risk alone were used as a guideline to design the acute risk data standardization function as presented in FIGS. 2A and 2B. The points where the odds ratio changes its slope (FIG. 2A) are natural cut points for a piecewise linear approximation of a standardization function (FIG. 2B).

Figure 3A:
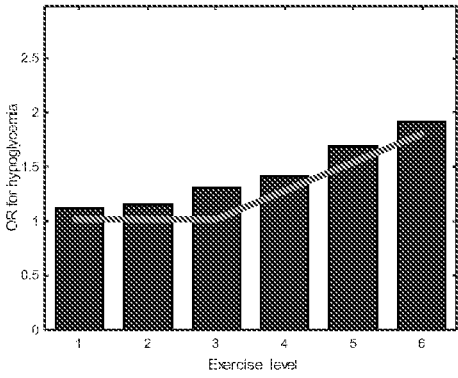
FIGS. 3A and 3B are exemplary graphs of odds ratio and standardization function for hypoglycemia based on exercise level.
Figure 3B:
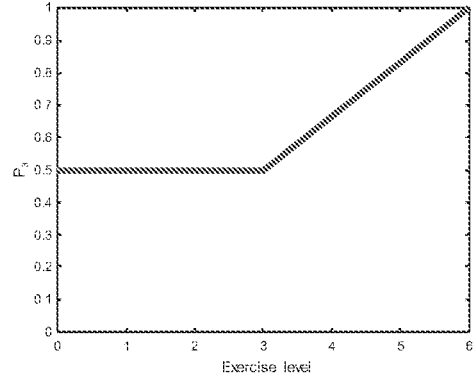

Standardization of Additional Signals: The mapping of data derived from additional signals, such as subjective ratings of recent physical activity, carbohydrate intake, or insulin delivery would depend on the specifics of each signal and on its relationship to upcoming hypoglycemia. However, the general mapping paradigm described above will hold: a change in the slope of the odds ratio for impending hypoglycemia would indicate a cutoff point of the linear function mapping the data onto probability for hypoglycemia. FIGS. 3A and 3B present an example of such a mapping that uses the data from the training data set to produce a probability for upcoming hypoglycemia based on a subjective rating of recent exercise rated on a scale from 0 (none) to 6 (more than usual). A subjective exercise rating is converted into probability for impending hypoglycemia using the change in the odds ratios observed in the training data (FIG. 3A). Because ratings below 3 indicate a relatively flat ratio for impending hypoglycemia, these ratings are mapped to 0.5—the uncertainty zone indicating neither lower nor higher risk for hypoglycemia.

Probability Aggregation from Multiple Data Sources: This is a stepwise procedure used to track dynamically the risk for hypoglycemia indicated from multiple data sources. The data aggregation follows a classical Bayes formula, and the update is done in steps whenever new information becomes available from any of the data sources.

Step 1—the procedure is initialized with each individual's Chronic using the probability mapping in FIG. 1B as follows:

$$P^1_{hypo} = P_1(eChronicRisk)$$

Step 2—if acute risk data is available, the probability for hypoglycemia is updated as follows:

$$P^2_{hypo} = \frac{P^1_{hypo} \cdot P_2(eAcuteRisk)}{P^1_{hypo} \cdot P_2(eAcuteRisk) + (1 - P^1_{hypo}) \cdot (1 - P_2(eAcuteRisk))}$$

Step 3 and all subsequent steps: if additional signals are available each is entered though it's standardized probability mapping (e.g. FIG. 3 as presented for exercise):

$$P^3_{hypo} = \frac{P^2_{hypo} \cdot P_3(\text{Exercise})}{P^2_{hypo} \cdot P_3(\text{Exercise}) + (1 - P^2_{hypo}) \cdot (1 - P_3(\text{Exercise}))}$$

Figure 10:
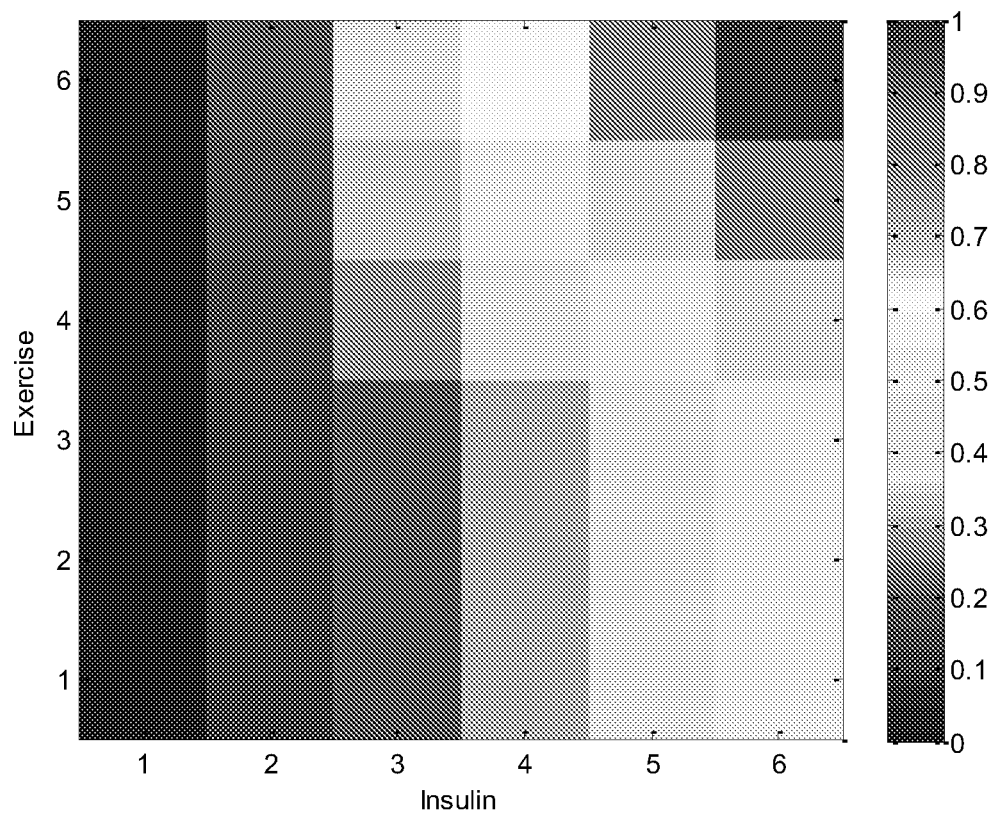
FIG. 10 an exemplary graph of odds ratios based on multiple dependent sources.

It is important to note here that this derivation relies on the independence of hypoglycemia from each data source, which allows to replace P(A and B) by P(A)*P(B). In the case where this independence may not be present (for example when food and insulin are added), the Exercise update step can be replace by a "Non-SMBG" step, that combines the dependent data sources, where the odd ratios are computed for the combination of the dependent sources (e.g. Exercise x Insulin) and P3 is derived in a multivariate manner as illustrated in FIG. 10.

Validation of the Tracking Procedure

Figure 4A:
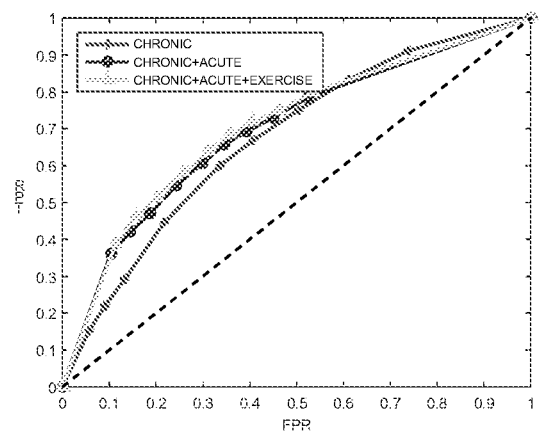
FIGS. 4A and 4B are graphs of Receiver Operating Characteristic curves for classifiers of upcoming hypoglycemia based on chronic risk alone.
Figure 4B:
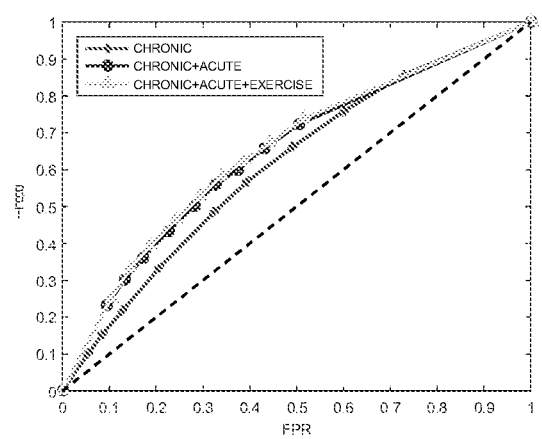

As noted above, all model parameters and steps of the method were developed and fixed using the training data sets of Studies 1 and 2 (see Available data). After that the procedure was fixed and applied prospectively to the independent test data set (Study 3). FIG. 4 presents ROC (Receiver Operating Characteristic) curves for classifiers of upcoming hypoglycemia based on Chronic risk alone, Chronic+Acute risk, and Chronic+Acute+Exercise risk, for the BG below 70 mg/dl (Panel A) and the BG below 50 mg/dl (Panel B). It is evident that the performance of the procedure in the independent test data set is virtually identical (even slightly better) than the performance in the training data used for its development, which indicates that the procedure could be generalized to any other data set. FIGS. 4A and 4B illustrate ROC curves for a classifier of upcoming hypoglycemia: BG<70 mg/dl (FIG. 4A) and BG<50mg/dl (FIG. 4B). Predictably, the ROC curvature (e.g. the performance of the procedure) increases with adding more data sources.

Table 1 presents the results of FIG. 4 in numerical format, displaying the odds ratios for impending hypoglycemia (defined as BG<70 mg/dl) at increasingly higher thresholds for the aggregated probability for hypoglycemia based on Chronic, Acute, and Exercise-related risks, in the training and in the test data. It is evident that an aggregated probability of 0.7 or above indicates in a 2-fold or higher likelihood for future hypoglycemia; thus, the dynamical risk tracking procedure works as intended.

TABLE 1

| Odds Ratio for Hypoglycemia | | |
| --- | --- | --- |
| P threshold | TRAINING | TEST DATA |
| 0.5 | 1.4403 | 1.5328 |
| 0.6 | 1.6661 | 1.7828 |
| 0.7 | 1.8631 | 1.9947 |
| 0.8 | 2.1014 | 2.1809 |
| 0.9 | 2.3702 | 2.2304 |

Figure 5:
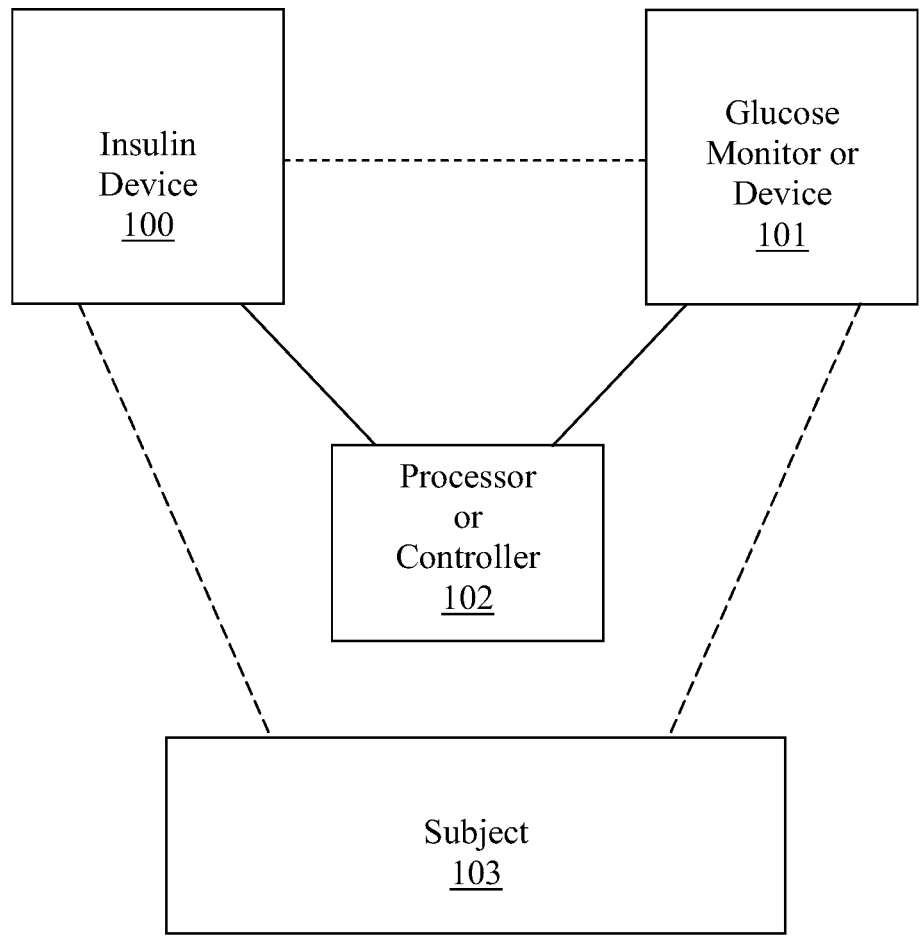
FIG. 5 is a high level functional block diagram of an embodiment of the present invention.

FIG. 5 is a high level functional block diagram of an embodiment of the present invention, or an aspect of an embodiment of the present invention.

As shown in FIG. 5, a processor or controller 102 communicates with the glucose monitor or device 101, and optionally the insulin device 100. The glucose monitor or device 101 communicates with the subject 103 to monitor glucose levels of the subject 103. The processor or controller 102 is configured to perform the required calculations. Optionally, the insulin device 100 communicates with the subject 103 to deliver insulin to the subject 103. The processor or controller 102 is configured to perform the required calculations. The glucose monitor 101 and the insulin device 100 may be implemented as a separate device or as a single device. The processor 102 can be implemented locally in the glucose monitor 101, the insulin device 100, or a standalone device (or in any combination of two or more of the glucose monitor, insulin device, or a stand along device). The processor 102 or a portion of the system can be located remotely such that the device is operated as a telemedicine device.

Figure 6A:
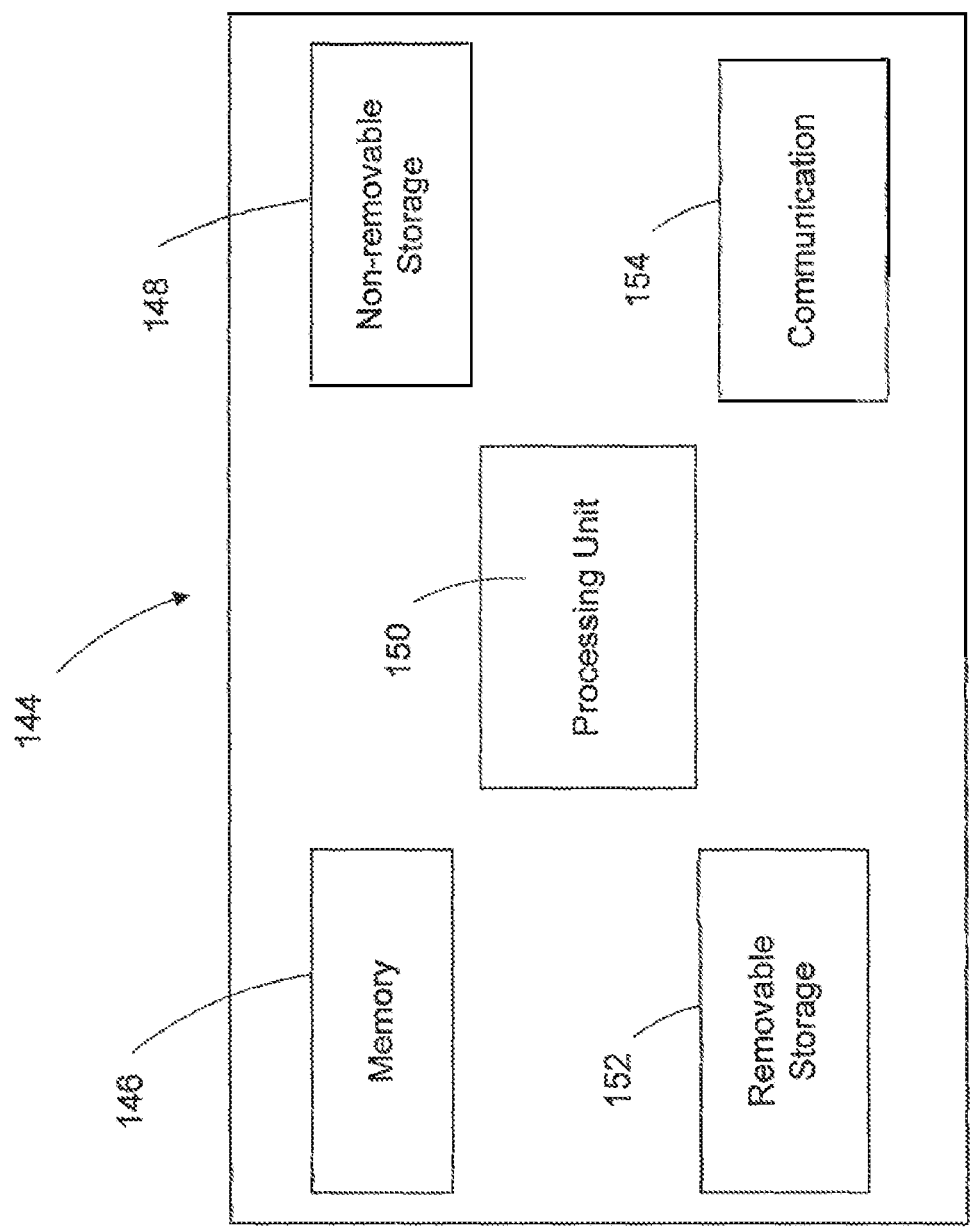
FIG. 6A is a high level functional block diagram of a computing device.

Referring to FIG. 6A, in its most basic configuration, computing device 144 typically includes at least one processing unit 150 and memory 146. Depending on the exact configuration and type of computing device, memory 146 can be volatile (such as RAM), non-volatile (such as ROM, flash memory, etc.) or some combination of the two.

Additionally, device 144 may also have other features and/or functionality. For example, the device could also include additional removable and/or non-removable storage including, but not limited to, magnetic or optical disks or tape, as well as writable electrical storage media. Such additional storage is the figure by removable storage 152 and non-removable storage 148. Computer storage media includes volatile and nonvolatile, removable and non-removable media implemented in any method or technology for storage of information such as computer readable instructions, data structures, program modules or other data. The memory, the removable storage and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device.

The device may also contain one or more communications connections 154 that allow the device to communicate with other devices (e.g. other computing devices). The communications connections carry information in a communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media.

Figure 6B:
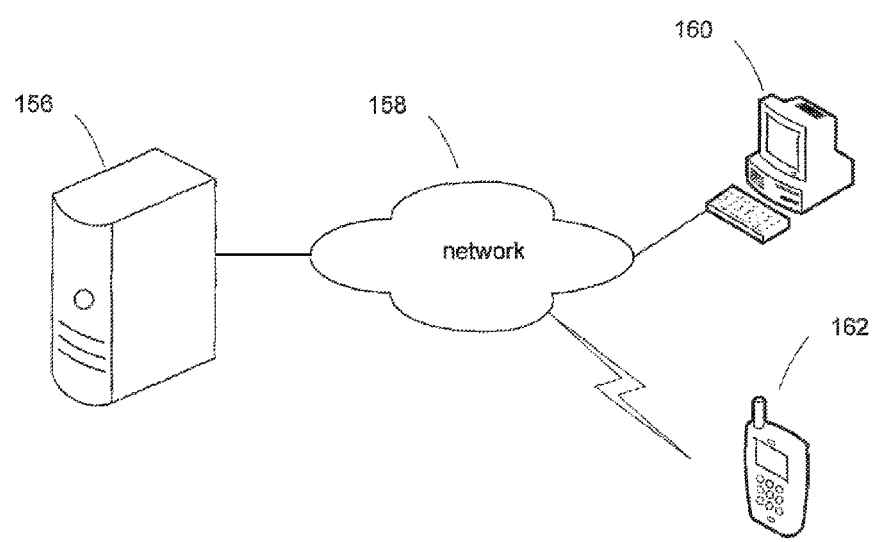
FIG. 6B is an exemplary network system in which embodiments of the present invention can be implemented.

In addition to a stand-alone computing machine, embodiments of the invention can also be implemented on a network system comprising a plurality of computing devices that are in communication with a networking means, such as a network with an infrastructure or an ad hoc network. The network connection can be wired connections or wireless connections. As a way of example, FIG. 6B illustrates a network system in which embodiments of the invention can be implemented. In this example, the network system comprises computer 156 (e.g. a network server), network connection means 158 (e.g. wired and/or wireless connections), computer terminal 160, and PDA (e.g. a smart-phone) 162 (or other handheld or portable device, such as a cell phone, laptop computer, tablet computer, GPS receiver, mp3 player, handheld video player, pocket projector, etc. or handheld devices (or non-portable devices) with combinations of such features). In an embodiment, it should be appreciated that the module listed as 156 may be glucose monitor device. In an embodiment, it should be appreciated that the module listed as 156 may be a glucose monitor device and/or an insulin device. Any of the components shown or discussed with FIG. 6B may be multiple in number. The embodiments of the invention can be implemented in anyone of the devices of the system. For example, execution of the instructions or other desired processing can be performed on the same computing device that is anyone of 156, 160, and 162. Alternatively, an embodiment of the invention can be performed on different computing devices of the network system. For example, certain desired or required processing or execution can be performed on one of the computing devices of the network (e.g. server 156 and/or glucose monitor device), whereas other processing and execution of the instruction can be performed at another computing device (e.g. terminal 160) of the network system, or vice versa. In fact, certain processing or execution can be performed at one computing device (e.g. server 156 and/or glucose monitor device); and the other processing or execution of the instructions can be performed at different computing devices that may or may not be networked. For example, the certain processing can be performed at terminal 160, while the other processing or instructions are passed to device 162 where the instructions are executed. This scenario may be of particular value especially when the PDA 162 device, for example, accesses to the network through computer terminal 160 (or an access point in an ad hoc network). For another example, software to be protected can be executed, encoded or processed with one or more embodiments of the invention. The processed, encoded or executed software can then be distributed to customers. The distribution can be in a form of storage media (e.g. disk) or electronic copy.

Figure 7:
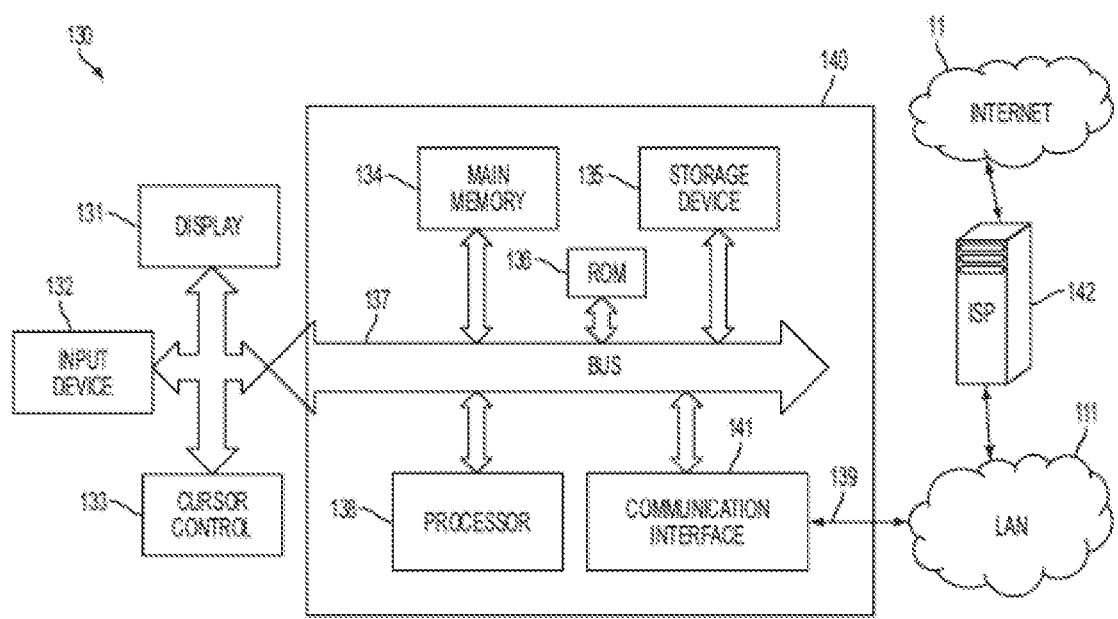
FIG. 7 is an exemplary block diagram of a system including a computer system and an internet connection.

FIG. 7 is a block diagram that illustrates a system 130 including a computer system 140 and the associated Internet 11 connection upon which an embodiment may be implemented. Such configuration is typically used for computers (hosts) connected to the Internet 11 and executing a server or a client (or a combination) software. A source computer such as laptop, an ultimate destination computer and relay servers, for example, as well as any computer or processor described herein, may use the computer system configuration and the Internet connection shown in FIG. 7. The system 140 may be used as a portable electronic device such as a notebook/laptop computer, a media player (e.g., MP3 based or video player), a cellular phone, a Personal Digital Assistant (PDA), a glucose monitor device, an insulin delivery device, an image processing device (e.g., a digital camera or video recorder), and/or any other handheld computing devices, or a combination of any of these devices. Note that while FIG. 7 illustrates various components of a computer system, it is not intended to represent any particular architecture or manner of interconnecting the components; as such details are not germane to the present invention. It will also be appreciated that network computers, handheld computers, cell phones and other data processing systems which have fewer components or perhaps more components may also be used. The computer system of FIG. 7 may, for example, be an Apple Macintosh computer or Power Book, or an IBM compatible PC. Computer system 140 includes a bus 137, an interconnect, or other communication mechanism for communicating information, and a processor 138, commonly in the form of an integrated circuit, coupled with bus 137 for processing information and for executing the computer executable instructions. Computer system 140 also includes a main memory 134, such as a Random Access Memory (RAM) or other dynamic storage device, coupled to bus 137 for storing information and instructions to be executed by processor 138.

Main memory 134 also may be used for storing temporary variables or other intermediate information during execution of instructions to be executed by processor 138. Computer system 140 further includes a Read Only Memory (ROM) 136 (or other non-volatile memory) or other static storage device coupled to bus 137 for storing static information and instructions for processor 138. A storage device 135, such as a magnetic disk or optical disk, a hard disk drive for reading from and writing to a hard disk, a magnetic disk drive for reading from and writing to a magnetic disk, and/or an optical disk drive (such as DVD) for reading from and writing to a removable optical disk, is coupled to bus 137 for storing information and instructions. The hard disk drive, magnetic disk drive, and optical disk drive may be connected to the system bus by a hard disk drive interface, a magnetic disk drive interface, and an optical disk drive interface, respectively. The drives and their associated computer-readable media provide non-volatile storage of computer readable instructions, data structures, program modules and other data for the general purpose computing devices. Typically computer system 140 includes an Operating System (OS) stored in a non-volatile storage for managing the computer resources and provides the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of operating systems are Microsoft Windows, Mac OS X, and Linux.

The term "processor" is meant to include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., silicon "die"), or distributed among two or more substrates. Furthermore, various functional aspects of the processor may be implemented solely as software or firmware associated with the processor.

Computer system 140 may be coupled via bus 137 to a display 131, such as a Cathode Ray Tube (CRT), a Liquid Crystal Display (LCD), a flat screen monitor, a touch screen monitor or similar means for displaying text and graphical data to a user. The display may be connected via a video adapter for supporting the display. The display allows a user to view, enter, and/or edit information that is relevant to the operation of the system. An input device 132, including alphanumeric and other keys, is coupled to bus 137 for communicating information and command selections to processor 138. Another type of user input device is cursor control 133, such as a mouse, a trackball, or cursor direction keys for communicating direction information and command selections to processor 138 and for controlling cursor movement on display 131. This input device typically has two degrees of freedom in two axes, a first axis (e.g., x) and a second axis (e.g., y), that allows the device to specify positions in a plane.

The computer system 140 may be used for implementing the methods and techniques described herein. According to one embodiment, those methods and techniques are performed by computer system 140 in response to processor 138 executing one or more sequences of one or more instructions contained in main memory 134. Such instructions may be read into main memory 134 from another computer-readable medium, such as storage device 135. Execution of the sequences of instructions contained in main memory 134 causes processor 138 to perform the process steps described herein. In alternative embodiments, hard-wired circuitry may be used in place of or in combination with software instructions to implement the arrangement. Thus, embodiments of the invention are not limited to any specific combination of hardware circuitry and software.

The term "computer-readable medium" (or "machine-readable medium") as used herein is an extensible term that refers to any medium or any memory, that participates in providing instructions to a processor, (such as processor 138) for execution, or any mechanism for storing or transmitting information in a form readable by a machine (e.g., a computer). Such a medium may store computer-executable instructions to be executed by a processing element and/or control logic, and data which is manipulated by a processing element and/or control logic, and may take many forms, including but not limited to, non-volatile medium, volatile medium, and transmission medium. Transmission media includes coaxial cables, copper wire and fiber optics, including the wires that comprise bus 137. Transmission media can also take the form of acoustic or light waves, such as those generated during radio-wave and infrared data communications, or other form of propagated signals (e.g., carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to processor 138 for execution. For example, the instructions may initially be carried on a magnetic disk of a remote computer. The remote computer can load the instructions into its dynamic memory and send the instructions over a telephone line using a modem. A modem local to computer system 140 can receive the data on the telephone line and use an infra-red transmitter to convert the data to an infra-red signal. An infra-red detector can receive the data carried in the infra-red signal and appropriate circuitry can place the data on bus 137. Bus 137 carries the data to main memory 134, from which processor 138 retrieves and executes the instructions. The instructions received by main memory 134 may optionally be stored on storage device 135 either before or after execution by processor 138.

Computer system 140 also includes a communication interface 141 coupled to bus 137. Communication interface 141 provides a two-way data communication coupling to a network link 139 that is connected to a local network 111. For example, communication interface 141 may be an Integrated Services Digital Network (ISDN) card or a modem to provide a data communication connection to a corresponding type of telephone line. As another non-limiting example, communication interface 141 may be a local area network (LAN) card to provide a data communication connection to a compatible LAN. For example, Ethernet based connection based on IEEE802.3 standard may be used such as 10/100BaseT, 1000BaseT (gigabit Ethernet), 10 gigabit Ethernet (10 GE or 10 GbE or 10 GigE per IEEE Std 802.3ae-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (June 1999), "Internetworking Technologies Handbook", Chapter 7: "Ethernet Technologies", pages 7-1 to 7-38, which is incorporated in its entirety for all purposes as if fully set forth herein. In such a case, the communication interface 141 typically include a LAN transceiver or a modem, such as Standard Microsystems Corporation (SMSC) LAN91C111 10/100 Ethernet transceiver described in the Standard Microsystems Corporation (SMSC) data-sheet "LAN91C111 10/100 Non-PCI Ethernet Single Chip MAC+ PHY" Data-Sheet, Rev. 15 (Feb. 20, 2004), which is incorporated in its entirety for all purposes as if fully set forth herein.

Wireless links may also be implemented. In any such implementation, communication interface 141 sends and receives electrical, electromagnetic or optical signals that carry digital data streams representing various types of information.

Network link 139 typically provides data communication through one or more networks to other data devices. For example, network link 139 may provide a connection through local network 111 to a host computer or to data equipment operated by an Internet Service Provider (ISP) 142. ISP 142 in turn provides data communication services through the world wide packet data communication network Internet 11. Local network 111 and Internet 11 both use electrical, electromagnetic or optical signals that carry digital data streams. The signals through the various networks and the signals on the network link 139 and through the communication interface 141, which carry the digital data to and from computer system 140, are exemplary forms of carrier waves transporting the information.

A received code may be executed by processor 138 as it is received, and/or stored in storage device 135, or other non-volatile storage for later execution. In this manner, computer system 140 may obtain application code in the form of a carrier wave.

The concept of dynamical tracking of the risk for hypoglycemia in type 1 and type 2 diabetes using multiple information have been developed and disclosed herein; and may be implemented and utilized with the related processors, networks, computer systems, internet, and components and functions according to the schemes disclosed herein.

Figure 8:
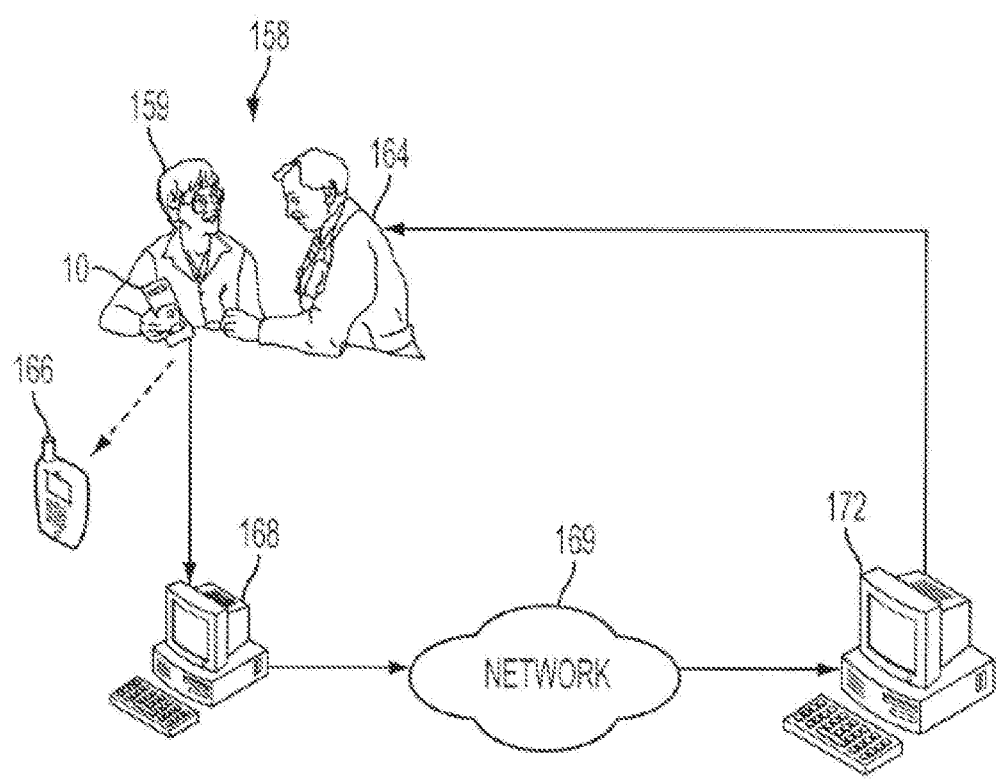
FIG. 8 is an exemplary system in which one or more embodiments of the invention can be implemented using a network.

FIG. 8 illustrates a system in which one or more embodiments of the invention can be implemented using a network, or portions of a network or computers. Although the present invention glucose device may be practiced without a network.

FIG. 8 diagrammatically illustrates an exemplary system in which examples of the invention can be implemented. In an embodiment the glucose monitor (and/or insulin pump) may be implemented by the subject (or patient) locally at home or other desired location. However, in an alternative embodiment it may be implemented in a clinic setting or assistance setting. For instance, referring to FIG. 8, a clinic setup 158 provides a place for doctors (e.g. 164) or clinician/assistant to diagnose patients (e.g. 159) with diseases related with glucose and related diseases and conditions. A glucose monitoring device 10 can be used to monitor and/or test the glucose levels of the patient—as a standalone device. It should be appreciated that while only glucose monitor device 10 is shown in the figure, the system of the invention and any component thereof may be used in the manner depicted by FIG. 8. The system or component may be affixed to the patient or in communication with the patient as desired or required. For example the system or combination of components thereof—including a glucose monitor device 10 (or other related devices or systems such as a controller, and/or an insulin pump, or any other desired or required devices or components)—may be in contact, communication or affixed to the patient through tape or tubing (or other medical instruments or components) or may be in communication through wired or wireless connections. Such monitor and/or test can be short term (e.g. clinical visit) or long term (e.g. clinical stay or family). The glucose monitoring device outputs can be used by the doctor (clinician or assistant) for appropriate actions, such as insulin injection or food feeding for the patient, or other appropriate actions or modeling. Alternatively, the glucose monitoring device output can be delivered to computer terminal 168 for instant or future analyses. The delivery can be through cable or wireless or any other suitable medium. The glucose monitoring device output from the patient can also be delivered to a portable device, such as PDA 166. The glucose monitoring device outputs with improved accuracy can be delivered to a glucose monitoring center 172 for processing and/or analyzing. Such delivery can be accomplished in many ways, such as network connection 170, which can be wired or wireless.

In addition to the glucose monitoring device outputs, errors, parameters for accuracy improvements, and any accuracy related information can be delivered, such as to computer 168, and/or glucose monitoring center 172 for performing error analyses. This can provide a centralized accuracy monitoring, modeling and/or accuracy enhancement for glucose centers, due to the importance of the glucose sensors.

Examples of the invention can also be implemented in a standalone computing device associated with the target glucose monitoring device. An exemplary computing device (or portions thereof) in which examples of the invention can be implemented is schematically illustrated in FIG. 6A.

Figure 9:
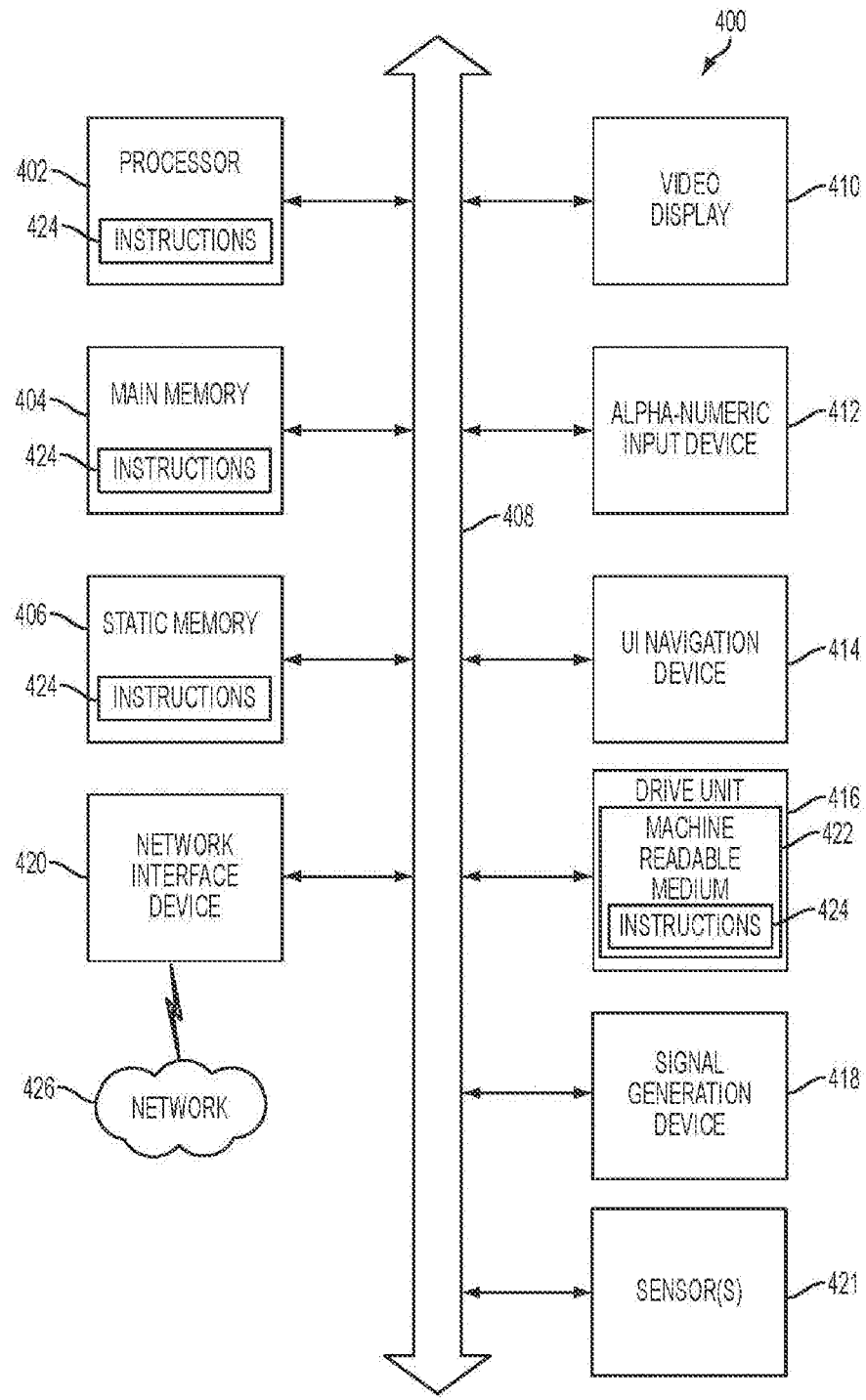
FIG. 9 is a block diagram of an exemplary machine upon which one or more aspects of the invention can be implemented.

FIG. 9 is a block diagram illustrating an example of a machine upon which one or more aspects of ebodiments of the present invention can be implemented.

FIG. 9 illustrates a block diagram of an example machine 400 upon which one or more embodiments (e.g., discussed methodologies) can be implemented (e.g., run).

Examples of machine 400 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 400) and software architectures that can be deployed in example embodiments.

In an example, the machine 400 can operate as a stand-alone device or the machine 400 can be connected (e.g., networked) to other machines.

In a networked deployment, the machine 400 can operate in the capacity of either a server or a client machine in server-client network environments. In an example, machine 400 can act as a peer machine in peer-to-peer (or other distributed) network environments. The machine 400 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 400. Further, while only a single machine 400 is illustrated, the term "machine" shall also be taken to include any collection of machines that individually or jointly execute a set (or multiple sets) of instructions to perform any one or more of the methodologies discussed herein.

Example machine (e.g., computer system) 400 can include a processor 402 (e.g., a central processing unit (CPU), a graphics processing unit (GPU) or both), a main memory 404 and a static memory 406, some or all of which can communicate with each other via a bus 408. The machine 400 can further include a display unit 410, an alphanumeric input device 412 (e.g., a keyboard), and a user interface (UI) navigation device 411 (e.g., a mouse). In an example, the display unit410, input device 412 and UI navigation device 414 can be a touch screen display. The machine 400 can additionally include a storage device (e.g., drive unit) 416, a signal generation device 418 (e.g., a speaker), a network interface device 420, and one or more sensors 421, such as a global positioning system (GPS) sensor, compass, accelerometer, or other sensor.

The storage device 416 can include a machine readable medium 422 on which is stored one or more sets of data structures or instructions 424 (e.g., software) embodying or utilized by any one or more of the methodologies or functions described herein. The instructions 424 can also reside, completely or at least partially, within the main memory 404, within static memory 406, or within the processor 402 during execution thereof by the machine 400. In an example, one or any combination of the processor 402, the main memory 404, the static memory 406, or the storage device 416 can constitute machine readable media.

While the machine readable medium 422 is illustrated as a single medium, the term "machine readable medium" can include a single medium or multiple media (e.g., a centralized or distributed database, and/or associated caches and servers) that configured to store the one or more instructions 424. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 424 can further be transmitted or received over a communications network 426 using a transmission medium via the network interface device 420 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

It should be appreciated that various sizes, dimensions, contours, rigidity, shapes, flexibility and materials of any of the components or portions of components in the various embodiments discussed throughout may be varied and utilized as desired or required. Similarly, locations and alignments of the various components may vary as desired or required.

It should be appreciated that any of the components or modules referred to with regards to any of the present invention embodiments discussed herein, may be integrally or separately formed with one another. Further, redundant functions or structures of the components or modules may be implemented.

It should be appreciated that the device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

REFERENCES

The following patents, applications and publications as listed below and throughout this document are hereby incorporated by reference in their entirety herein. It should be appreciated that various aspects of embodiments of the present method, system, devices, article of manufacture, computer readable medium, and compositions may be implemented with the following methods, systems, devices, article of manufacture, computer readable medium, and compositions disclosed in the following U.S. Patent Applications, U.S. Patents, and PCT International Patent Applications and are hereby incorporated by reference herein and co-owned with the assignee (and which are not admitted to be prior art with respect to the present invention by inclusion in this section):

U.S. patent application Ser. No. 14/419,375 entitled "Computer Simulation for Testing and Monitoring of Treatment Strategies for Stress Hyperglycemia", filed Feb. 3, 2015.

International Patent Application No. PCT/US2013/053664 entitled "Computer Simulation for Testing and Monitoring of Treatment Strategies for Stress Hyperglycemia", filed Aug. 5, 2013; International Patent Application Publication No. WO 2014/022864, Feb. 6, 2014.

International Patent Application No. PCT/US2015/010167 entitled "Central Data Exchange Node For System Monitoring and Control of Blood Glucose Levels in Diabetic Patients", filed Jan. 5, 2015.

International Patent Application No. PCT/US2014/045393 entitled "Simulation of Endogenous and Exogenous Glucose/Insulin/Glucagon Interplay in Type 1 Diabetic Patients", filed Jul. 3, 2014; International Patent Application Publication No. WO 2015/003124, Jan. 8, 2015.

U.S. patent application Ser. No. 14/266,612 entitled "Method, System and Computer Program Product for Real-Time Detection of Sensitivity Decline in Analyte Sensors", filed Apr. 30, 2014; U.S. Patent Application Publication No. 2014/0244216, Aug. 28, 2014.

U.S. patent application Ser. No. 13/418,305 entitled "Method, System and Computer Program Product for Real-Time Detection of Sensitivity Decline in Analyte Sensors", filed Mar. 12, 2012; U.S. Pat. No. 8,718,958, issued May 6, 2014.

International Patent Application No. PCT/US2007/082744 entitled "Method, System and Computer Program Product for Real-Time Detection of Sensitivity Decline in Analyte Sensors", filed Oct. 26, 2007; International Patent Application Publication No. WO/2008/052199, May 2, 2008.

U.S. patent application Ser. No. 11/925,689 entitled "Method, System and Computer Program Product for Real-Time Detection of Sensitivity Decline in Analyte Sensors", filed Oct. 26, 2007; U.S. Pat. No. 8,135,548, issued Mar. 13, 2012.

U.S. patent application Ser. No. 14/241,383 entitled "Method, System and Computer Readable Medium for Adaptive Advisory Control of Diabetes", filed Feb. 26, 2014. International Patent Application No. PCT/US2012/052422 entitled "Method, System and Computer Readable Medium for Adaptive Advisory Control of Diabetes", filed Aug. 26, 2012; International Patent Application Publication No. WO 2013/032965, Mar. 7, 2013.

International Patent Application No. PCT/US2014/017754 entitled "Method and System for Model-Based Tracking of Changes in Average Glycemia in Diabetes", filed Feb. 21, 2014; International Patent Application Publication No. WO 2014/130841, Aug. 28, 2014.

U.S. patent application Ser. No. 14/128,922 entitled "Unified Platform For Monitoring and Control of Blood Glucose Levels in Diabetic Patients", filed Dec. 23, 2013; U.S. Patent Application Publication No. 2015/0018633, Jan. 15, 2015.

International Patent Application No. PCT/US2012/043910 entitled "Unified Platform For Monitoring and Control of Blood Glucose Levels in Diabetic Patients", filed Jun. 23, 2012; International Patent Application Publication No. WO 2012/178134, Dec. 27, 2012.

U.S. patent application Ser. No. 14/128,811 entitled "Methods and Apparatus for Modular Power Management and Protection of Critical Services in Ambulatory Medical Devices", filed Dec. 23, 2013; U.S. Patent Application Publication No. 2014/0215239, Jul. 31, 2014.

International Patent Application No. PCT/US2012/043883 entitled "Methods and Apparatus for Modular Power Management and Protection of Critical Services in Ambulatory Medical Devices", filed Jun. 22, 2012; International Patent Application Publication No. WO 2012/178113, Dec. 27, 2012.

U.S. patent application Ser. No. 14/015,831 entitled "CGM-Based Prevention of Hypoglycemia Via Hypoglycemia Risk Assessment and Smooth Reduction Insulin Delivery", filed Aug. 30, 2013; U.S. Patent Application Publication No. 2014/0046159, Feb. 13, 2014.

U.S. patent application Ser. No. 13/203,469 entitled "CGM-Based Prevention of Hypoglycemia via Hypoglycemia Risk Assessment and Smooth Reduction Insulin Delivery", filed Aug. 25, 2011; U.S. Pat. No. 8,562,587, issued Oct. 22, 2013.

International Patent Application No. PCT/US2010/025405 entitled "CGM-Based Prevention of Hypoglycemia via Hypoglycemia Risk Assessment and Smooth Reduction Insulin Delivery", filed Feb. 25, 2010; International Patent Application Publication No. WO 2010/099313, Sep. 2, 2010.

International Patent Application No. PCT/US2013/042745 entitled "Insulin-Pramlintide Compositions and Methods for Making and Using Them", filed May 24, 2013; International Application Publication No. WO 2013/177565, Nov. 28, 2013.

U.S. patent application Ser. No. 13/637,359 entitled "Method, System, and Computer Program Product for Improving the Accuracy of Glucose Sensors Using Insulin Delivery Observation in Diabetes", filed Sep. 25, 2012; U.S. Patent Application Publication No. 2013/0079613, Mar. 28, 2013.

International Patent Application No. PCT/US2011/029793 entitled "Method, System, and Computer Program Product for Improving the Accuracy of Glucose Sensors Using Insulin Delivery Observation in Diabetes", filed Mar. 24, 2011; International Patent Application Publication No. WO 2011/119832, Sep. 29, 2011.

U.S. patent application Ser. No. 13/634,040 entitled "Method and System for the Safety, Analysis, and Supervision of Insulin Pump Action and Other Modes of Insulin Delivery in Diabetes", filed Sep. 11, 2012; U.S. Patent Application Publication No. 2013/0116649, May 9, 2013.

International Patent Application No. PCT/US2011/028163 entitled "Method and System for the Safety, Analysis, and Supervision of Insulin Pump Action and Other Modes of Insulin Delivery in Diabetes", filed Mar. 11, 2011; International Patent Application Publication No. WO 2011/112974, Sep. 15, 2011. U.S. patent application Ser. No. 13/394,091 entitled "Tracking the Probability for Imminent Hypoglycemia in Diabetes from Self-Monitoring Blood Glucose (SMBG) Data", filed Mar. 2, 2012; U.S. Patent Application Publication No. 2012/0191361, Jul. 26, 2012.

International Patent Application No. PCT/US2010/047711 entitled "Tracking the Probability for Imminent Hypoglycemia in Diabetes from Self-Monitoring Blood Glucose (SMBG) Data", filed Sep. 2, 2010; International Patent Application Publication No. WO 2011/028925, Mar. 10, 2011.

U.S. patent application Ser. No. 13/393,647 entitled "System, Method and Computer Program Product for Adjustment of Insulin Delivery (AID) in Diabetes Using Nominal Open-Loop Profiles", filed Mar. 1, 2012; U.S. Patent Application Publication No. 2012/0245556, Sep. 27, 2012.

International Patent Application No. PCT/US2010/047386 entitled "System, Method and Computer Program Product for Adjustment of Insulin Delivery (AID) in Diabetes Using Nominal Open-Loop Profiles", filed Aug. 31, 2010; International Application Publication No. WO 2011/028731, Mar. 10, 2011.

U.S. patent application Ser. No. 13/380,839 entitled "System, Method, and Computer Simulation Environment for In Silico Trials in Pre-Diabetes and Type 2 Diabetes", filed Dec. 25, 2011; U.S. Patent Application Publication No. 2012/0130698, May 24, 2012.

International Patent Application No. PCT/US2010/040097 entitled "System, Method, and Computer Simulation Environment for In Silico Trials in Prediabetes and Type 2 Diabetes", filed Jun. 25, 2010; International Application Publication No. WO 2010/151834, Dec. 29, 2010.

U.S. patent application Ser. No. 13/322,943 entitled "System Coordinator and Modular Architecture for Open-Loop and Closed-Loop Control of Diabetes", filed Nov. 29, 2011; U.S. Patent Application Publication No. 2012/0078067, Mar. 29, 2012.

International Patent Application No. PCT/US2010/036629 entitled "System Coordinator and Modular Architecture for Open-Loop and Closed-Loop Control of Diabetes", filed May 28, 2010; International Patent Application Publication No. WO 2010/138848, Dec. 2, 2010.

U.S. patent application Ser. No. 13/131,467 entitled "Method, System, and Computer Program Product for Tracking of Blood Glucose Variability in Diabetes", filed May 26, 2011; U.S. Patent Application Publication No. 2011/0264378, Oct. 27, 2011.

International Patent Application No. PCT/US2009/065725 entitled "Method, System, and Computer Program Product for Tracking of Blood Glucose Variability in Diabetes", filed Nov. 24, 2009; International Patent Application Publication No. WO 2010/062898, Jun. 3, 2010.

U.S. patent application Ser. No. 12/975,580 entitled "Method, System, and Computer Program Product for the Evaluation of Glycemic Control in Diabetes from Self-Monitoring Data", filed Dec. 22, 2010; U.S. Patent Application Publication No. 2012/0004512, Jan. 5, 2012.

U.S. patent application Ser. No. 11/305,946 entitled "Method, System, and Computer Program Product for the Evaluation of Glycemic Control in Diabetes from Self-Monitoring Data", filed Dec. 19, 2005; U.S. Pat. No. 7,874,985, issued Jan. 25, 2011.

U.S. patent application Ser. No. 10/240,228 entitled "Method, System, and Computer Program Product for the Evaluation of Glycemic Control in Diabetes from Self-Monitoring Data", filed Sep. 26, 2002; U.S. Pat. No. 7,025,425, issued Apr. 11, 2006.

International Patent Application No. PCT/US2001/009884 entitled "Method, System, and Computer Program Product for the Evaluation of Glycemic Control in Diabetes", filed Mar. 29, 2001; International Application Publication No. WO 2001/72208, Oct. 4, 2001.

U.S. patent application Ser. No. 12/674,348 entitled "Method, Computer Program Product and System for Individual Assessment of Alcohol Sensitivity", filed Feb. 19, 2010; U.S. Patent Application Publication No. 2011/0264374, Oct. 27, 2011.

U.S. patent application Ser. No. 12/665,149 entitled "Method, System and Computer Program Product for Evaluation of Insulin Sensitivity, Insulin/Carbohydrate Ratio, and Insulin Correction Factors in Diabetes from Self-Monitoring Data", filed Dec. 17, 2009; U.S. Patent Application Publication No. 2010/0198520, Aug. 5, 2010.

International Patent Application No. PCT/US2008/069416 entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008; International Patent Application Publication No. WO 2009/009528, Jan. 15, 2009.

U.S. patent application Ser. No. 12/664,444 entitled "Method, System and Computer Simulation Environment for Testing of Monitoring and Control Strategies in Diabetes", filed Dec. 14, 2009; U.S. Patent Application Publication No. 2010/0179768, Jul. 15, 2010.

International Patent Application No. PCT/US2008/067725 entitled "Method, System and Computer Simulation Environment for Testing of Monitoring and Control Strategies in Diabetes", filed Jun. 20, 2008; International Patent Application Publication No. WO 2008/157781, Dec. 24, 2008.

U.S. patent application Ser. No. 12/516,044 entitled "Method, System, and Computer Program Product for the Detection of Physical Activity by Changes in Heart Rate, Assessment of Fast Changing Metabolic States, and Applications of Closed and Open Control Loop in Diabetes", filed May 22, 2009; U.S. Pat. No. 8,585,593, issued Nov. 19, 2013.

International Patent Application No. PCT/US2007/085588 entitled "Method, System, and Computer Program Product for the Detection of Physical Activity by Changes in Heart Rate, Assessment of Fast Changing Metabolic States, and Applications of Closed and Open Control Loop in Diabetes", filed Nov. 27, 2007; International Patent Application Publication No.

U.S. patent application Ser. No. 12/159,891 entitled "Method, System and Computer Program Product for Evaluation of Blood Glucose Variability in Diabetes from Self-Monitoring Data", filed Jul. 2, 2008; U.S. Patent Application Publication 2009/0171589, Jul. 2, 2009.

International Patent Application No. PCT/US2007/000370 entitled "Method, System and Computer Program Product for Evaluation of Blood Glucose Variability in Diabetes from Self-Monitoring Data", filed Jan. 5, 2007; International Application Publication No. WO 2007/081853, Jul. 19, 2007.

U.S. patent application Ser. No. 12/065,257 entitled "Accuracy of Continuous Glucose Sensors", filed Feb. 28, 2008; U.S. Patent Application Publication No. 2008/0314395, Dec. 25, 2008.

International Patent Application No. PCT/US2006/033724 entitled "Method for Improvising Accuracy of Continuous Glucose Sensors and a Continuous Glucose Sensor Using the Same", filed Aug. 29, 2006; International Application Publication No. WO 2007027691, Mar. 8, 2007.

U.S. patent application Ser. No. 11/943,226 entitled "Systems, Methods and Computer Program Codes for Recognition of Patterns of Hyperglycemia and Hypoglycemia, Increased Glucose Variability, and Ineffective Self-Monitoring in Diabetes", filed Nov. 20, 2007; U.S. Patent Application Publication No. 2008/0154513, Jun. 26, 2008.

U.S. patent application Ser. No. 11/578,831 entitled "Method, System and Computer Program Product for Evaluating the Accuracy of Blood Glucose Monitoring Sensors/Devices", filed Oct. 18, 2006; U.S. Pat. No. 7,815,569, issued Oct. 19, 2010.

International Patent Application No. U52005/013792 entitled "Method, System and Computer Program Product for Evaluating the Accuracy of Blood Glucose Monitoring Sensors/Devices", filed Apr. 21, 2005; International Application Publication No. WO 2005/106017, Nov. 10, 2005.

U.S. patent application Ser. No. 10/524,094 entitled "Method, System, And Computer Program Product For The Processing Of Self-Monitoring Blood Glucose (SM BG) Data To Enhance Diabetic Self-Management", filed Feb. 9, 2005; U.S. Pat. No. 8,538,703, issued Sep. 17, 2013

International Patent Application No. PCT/US2003/025053 entitled "Managing and Processing Self-Monitoring Blood Glucose", filed Aug. 8, 2003; International Application Publication No. WO 2001/72208, Oct. 4, 2001.

International Patent Application No. PCT/US2002/005676 entitled "Method and Apparatus for the Early Diagnosis of Subacute, Potentially Catastrophic Illness", filed Feb. 27, 2002; International Application Publication No. WO 2002/67776, Sep. 6, 2002.

U.S. patent application Ser. No. 10/069,674 entitled "Method and Apparatus for Predicting the Risk of Hypoglycemia", filed Feb. 22, 2002; U.S. Pat. No. 6,923,763, issued Aug. 2, 2005.

International Patent Application No. PCT/US00/22886 entitled "METHOD AND APPARATUS FOR PREDICT- ING THE RISK OF HYPOGLYCEMIA", filed Aug. 21, 2000; International Application Publication No. WO 2001/13786, Mar. 1, 2001.

The following patents, applications and publications as listed below and throughout this document are hereby incorporated by reference in their entirety herein.

1. The Diabetes Control and Complications Trial Research Group. The effect of intensive treatment of diabetes on the development and progression of long-term complications of insulin-dependent diabetes mellitus. *N Engl J Med* 329: 978-986, 1993
2. The Diabetes Control and Complications Trial Research Group: The relationship of glycemic exposure (HbA1c) to the risk of development and progression of retinopathy in the Diabetes Control and Complications Trial. *Diabetes* 44:968-983, 1995.
3. Lachin J M, Genuth S, Nathan D M, Zinman B, Rutledge B N, DCCT/EDIC Research Group: Effect of Glycemic Exposure on the Risk of Microvascular Complications in the Diabetes Control and Complications Trial Revisited. *Diabetes,* 57: 995-1001, 2008.
4. Reichard P, Phil M. Mortality and treatment side effects during long-term intensified conventional insulin treatment in the Stockholm Diabetes Intervention study. *Diabetes* 43: 313-317, 1994
5. UK Prospective Diabetes Study Group (UKPDS). Intensive blood-glucose control with sulphonylureas or insulin compared with conventional treatment and risk of complications in patients with type 2 diabetes. Lancet 352: 837-853, 1998
6. Aaby Svendsen P, Lauritzen T, Soegard U, Nerup J. Glycosylated Haemoglobin and Steady-State Mean Blood Glucose Concentration in Type 1 (Insulin-Dependent) Diabetes. *Diabetologia,* 23: 403-405, 1982.
7. Santiago J V. Lessons from the Diabetes Control and Complications Trial, *Diabetes,* 42:1549-1554, 1993.
8. The Diabetes Control and Complications Trial Research Group. Hypoglycemia in the Diabetes Control and Complications Trial. *Diabetes* 46: 271-286, 1997
9. Henderson J N, Allen K V, Deary L I, Frier B M. Hypoglycemia in insulin-treated Type 2 diabetes: frequency, symptoms and impaired awareness. *Diabet Med* 20: 1016-1021, 2003
10. Gold A E, Frier B M, MacLeod K M, Deary I J. A structural equation model for predictors of severe hypoglycaemia in patients with insulin-dependent diabetes mellitus. *Diabet Med,* 14:309-315, 1997.
11. Cox D J, Kovatchev B, Julian D, Gonder-Frederick L A, Polonsky W H, Schlundt D G, Clarke W L.
Frequency of severe hypoglycemia in IDDM can be predicted from self-monitoring blood glucose data. *J Clin Endocrinol Metab* 79: 1659-1662, 1994.
12. Kovatchev B P, Cox D J, Gonder-Frederick L A Young-Hyman D, Schlundt D, Clarke W L. Assessment of risk for severe hypoglycemia among adults with IDDM: Validation of the Low Blood Glucose Index, *Diabetes Care* 21: 1870-1875, 1998.
13. Kovatchev B P, Cox D J, Kumar A, Gonder-Frederick L A and W L Clarke. Algorithmic Evaluation of Metabolic Control and Risk of Severe Hypoglycemia in Type 1 and Type 2 Diabetes Using Self-Monitoring Blood Glucose (SMBG) Data. *Diabetes Technol Ther,* 5 (5): 817-828, 2003.
14. Cox D J, Gonder-Frederick L A, Ritterband L, Clarke W L, and Kovatchev B P. Prediction of Severe Hypoglycemia. *Diabetes Care,* 30: 1370-1373, 2007.
15. Amiel S A, Sherwin R S, Simonson D C, Tamborlane W V. Effect of intensive insulin therapy on glycemic thresholds for counterregulatory hormone release. *Diabetes* 37: 901-907, 1988.
16. Amiel, S A, Tamborlane, W V, Simonson, D C and Sherwin, R S. Defective glucose counterregulation after strict glycemic control of insulin-dependent diabetes mellitus. *N Engl J Med* 316: 1376-1383, 1987.
17. Cryer P E, Gerich J E. Glucose counterregulation, hypoglycemia, and intensive therapy of diabetes mellitus. *N Engl J Med* 313: 232-241, 1985.
18. White N H, Skor D A, Cryer P E, Levandoski L, Santiago J V. Identification of type I diabetic patients at increased risk for hypoglycemia during intensive therapy. *N Eng/J Med* 308: 485-491, 1983.
19. Cryer PE. Iatrogenic hypoglycemia as a cause of hypoglycemia-associated autonomic failure in IDDM: A vicious cycle. *Diabetes* 41:255-260, 1992.
20. Henderson JN, Allen K V, Deary L I, Frier B M. Hypoglycemia in insulin-treated Type 2 diabetes: frequency, symptoms and impaired awareness. *Diabet Med* 20: 1016-1021, 2003.
21. Cryer P E. Hypoglycemia. Pathophysiology, Diagnosis and Treatment. Oxford University Press: New York, 1997.
22. Cryer P E, Davis S N, Shamoon H. Hypoglycemia in Diabetes. *Diabetes Care,* 26: 1902-1912, 2003.
23. American Diabetes Association Workgroup on Hypoglycemia (Childs B P, Clark N G, Cox D J, Cryer P E, Davis S N, Di-Nardo M M, Kahn R, Kovatchev B P, Shamoon H). Defining and Reporting Hypoglycemia in Diabetes. *Diabetes Care,* 28:1245-1249, 2005.
24. Cryer P E. Hypoglycaemia: The limiting factor in the glycaemic management of type I and type II diabetes. *Diabetologia* 45: 937-948, 2002
25. Cryer P E: Hypoglycemia: The Limiting factor in the management of IDDM. *Diabetes* 43: 1378-1389, 1994
26. Clarke WL, Cox D, Gonder-Frederick L A, Carter W, Pohl S L. Evaluating the clinical accuracy of self-blood glucose monitoring systems. *Diabetes Care,* 10: 622-628, 1987.
27. The diabetes research in children network (DirecNet) study group. A multicenter study of the accuracy of the One Touch® Ultra® home glucose meter in children with Type 1 diabetes. *Diabetes Technol Ther,* 5: 933-942, 2003
28. Hirsch I B, Bode B W, Childs B P, Close K L, Fisher W A, Gavin JR III, Ginsberg B H, Raine C H III, and Verderese CA. *Diabetes Technol Ther* 10: 419-439, 2008.
29. Freckmann G, Baumstark A, Jendrike N, Zschornack E, Kocher S, Tshiananga J, Heister F, and Haug C. System Accuracy Evaluation of 27 Blood Glucose Monitoring Systems According to DIN EN ISO 15197. *Diabetes Technol Ther* 12: 221-231, 2010.
30. Kovatchev B P, Flacke F, Sieber J, Breton M D. Accuracy and Robustness of Dynamical Tracking of Average Glycemia (A1c) to Provide Real-Time Estimation of Hemoglobin A1c Using Routine Self-Monitored Blood Glucose Data. *Diabetes Technol Ther* 2014; 16:303-309.
31. Nathan D M, Kuenen J, Borg R, Zheng H, Schoenfeld D, Heine R J: Translating the A1C assay into estimated average glucose values. *Diabetes Care* 2008 ;31:1473-1478.
32. Hamren B, Bjork E, Sunzel M, Karlsson M: Models for plasma glucose, HbA1c, and hemoglobin interrelationships in patients with type 2 diabetes following tesaglitazar treatment. *Clin Pharmacol Ther* 2008; 84:228-235.

33. Heisler M, Piette J D, Spencer M, Kieffer E, Vijan S: The relationship between knowledge of recent HbA1c values and diabetes care understanding and self-management. *Diabetes Care* 2005; 28:816-822.
34. Polneau S V, Lasserre V, Fonfrede M, Delattre J, Benazeth S: A different approach to analyzing age-related HbA1c values in non-diabetic subjects. Clinical Chemistry and Laboratory Medicine 2004; 42:423-428.
35. Landgraf R: The relationship of postprandial glucose to HbA1c. Diabetes Metab Res Rev 2004; 20 Suppl 2:S9-S12.
36. Kahrom M: An innovative mathematical model: a key to the riddle of HbA(1c). Int J Endocrinol 2010. 10.1155/2010/481326. Epub August 29.
37. Ollerton R L, Luzio S D, Owens D R: Contribution of fasting and postprandial plasma glucose to HbA1c. Diabet Med 2005; 22:954-955.
38. Osterman-Golkar S M, Vesper H W: Assessment of the relationship between glucose and A1c using kinetic modeling. J Diabetes Complications 2006; 20:285-294.
39. Trevino G: On the weighted-average relationship between plasma glucose and HbA1c. Diabetes Care 2006; 29:466-467.
40. Trevino G: A nonlinear relation between glucose and A1c. Diabetes Res Clin Pract 2008; 79:e14.
41. Hempe J M, Soros A A, Chalew SA. Estimated Average Glucose and Self-Monitored Mean Blood Glucose Are Discordant Estimates of Glycemic Control. Diabetes Care 2010; 33:1449-1451.
42. McCarter R J, Hempe J M, Gomez R, Chalew S A. Biological Variation in HbA1c Predicts Risk of Retinopathy and Nephropathy in Type 1 Diabetes. Diabetes Care 2004; 27:1259-1264.
43. Hempe J M, Liu S, Myers L, McCarter R J, Buse J B, and Fonseca V. The hemoglobin glycation index identifies subpopulations with harms or benefits from intensive treatment in the ACCORD trial. Diabetes Care Publish Ahead of Print, 2015. DOI: 10.2337/dc14-1844
44. Kovatchev B P, Straume M, Cox D J, Farhy L S. Risk analysis of blood glucose data: A quantitative approach to optimizing the control of insulin dependent diabetes. *J of Theor Med*, 3:1-10, 2001.
45. Kovatchev B P, Cox D J, Farhy L S, Straume M, Gonder-Frederick L A, Clarke, W L. Episodes of Severe Hypoglycemia in Type 1 Diabetes are Preceded, and Followed, within 48 Hours by Measurable Disturbances in Blood Glucose. *J Clin Endocrinol Metab*, 85: 4287-4292, 2000.
46. Kovatchev B P, Cox D J, Gonder-Frederick L A and W L Clarke. Symmetrization of the blood glucose measurement scale and its applications. *Diabetes Care*, 20: 1655-1658, 1997.
47. American Diabetes Association Workgroup on Hypoglycemia. Defining and Reporting Hypoglycemia in Diabetes. *Diabetes Care*, 28:1245-1249, 2005
48. Gerich J E, Langlois M, Noacco C, Karam J H, Forsham P H. Lack of glucagon response to hypoglycemia in diabetes: Evidence for an intrinsic pancreatic alpha cell defect. *Science* 182:171-173, 1973
49. Ovalle F, Fanelli C G, Paramore D S, Hershey T, Craft S, Cryer P E. Brief twice weekly episodes of hypoglycemia reduce detection of clinical hypoglycemia in type 1 diabetes mellitus. *Diabetes* 47:1472-1479, 1998
50. Kovatchev B P, Moorman J R, Clarke W L, Straume M. Method and apparatus for predicting the risk of hypoglycemia, U.S. Pat. No. 6,923,763 B1 issued on Aug. 2, 2005;
51. Gonder-Frederick L A, Cox D J, Kovatchev B P, Schlundt D, Clarke WL (1997). A Biopsychobehavioral Model of Risk of Severe Hypoglycemia. *Diabetes Care,* 20: 661-669.
52. Clarke W L, Cox D J, Gonder-Frederick L A, Julian D M, Kovatchev B P, Young-Hyman D (1999). The Bio-Psycho-Behavioral Model of Severe Hypoglycemia II: Self-Management Behaviors. *Diabetes Care,* 22: 580-584.
53. Cox D J, Gonder-Frederick L, Ritterband L, Patel K, Schachinger H, Fehm-Wolfsdorf G, Hermanns N, Snoek F, Zrebiec J, Polonsky W, Schlundt D, Kovatchev B, Clarke W (2006). Blood glucose awareness training: what is it, where is it, and where is it going? *Diabetes Spectrum,* 19: 43-49.
54. Kovatchev B P, Mendosa P, Anderson S M, Hawley J S, Ritterband L M, Gonder-Frederick L (2011).

Effect of automated bio-behavioral feedback on the control of type 1 diabetes. Diabetes Care, 34: 302-307.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the disclosure, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

What is claimed is:

1. A method for tracking hypoglycemia risk comprising:
   determining, for each of a plurality of intermittently available data sources, one or more probability signals for impending hypoglycemia, wherein each probability signal for an available data source is based on one or more inputs from the available data sources and each probability signal for an unavailable data source is based on a lack of input from the unavailable data source and assigned a value corresponding to a zone of uncertainty of risk of hypoglycemia; and
   determining an aggregate risk of hypoglycemia based on the plurality of intermittently available data sources by aggregating the plurality of probability signals;
   wherein at least one data source of the plurality of intermittently available data sources comprises continuous glucose monitoring (CGM) data.

2. The method of claim 1, wherein determining the plurality of probability signals for impending hypoglycemia includes determining a chronic risk of hypoglycemia based on the CGM data by the formulas $$eChronicRisk(t_0) = f_{Chronic}(CGM_{t_0})$$
$$eChronicRisk(t) = \beta 2 \cdot eChronicRisk(t-1) + \beta 1 \cdot f_{Chronic}(CGM_t)$$

wherein $\beta 1$ and $\beta 2$ are predefined constants.

3. The method of claim 1, wherein determining the plurality of probability signals for impending hypoglycemia includes determining an acute risk of hypoglycemia based on the CGM data by the formulas $$eAcuteRisk(t_0) = \alpha 1 \cdot f_{Acute}(CGM_{t_0})$$
$$eAcuteRisk(t) = \alpha 2 \cdot eAcuteRisk(t-1) + \alpha 1 \cdot f_{Acute}(CGM_t)$$

wherein $\alpha 1$ and $\alpha 2$ are predefined constants.

4. The method of claim 1, wherein the plurality of intermittently available data sources includes one or more of: a physical activity indication, an insulin delivery indication, a carbohydrate indication, and a non-insulin medicine indication.

5. The method of claim 4, wherein the physical activity indication comprises a signal from at least one sensor configured to detect when the user begins to exercise.

6. The method of claim 1, wherein one or more of the plurality of intermittently available data sources are automatically monitored and reported.

7. The method of claim 1, wherein one or more of the plurality of intermittently available data sources are self-reported by a user.

8. The method of claim 1, wherein determining a plurality of probability signals for impending hypoglycemia comprises translating each input from the available data sources into the probability signal for impending hypoglycemia.

9. The method of claim 1, wherein the probability signal for impending hypoglycemia is standardized on a scale where minimal risk of hypoglycemia is mapped to zero, maximal risk of hypoglycemia is mapped to 1, a cutoff value differentiating no-risk and elevated risk is mapped to 0.5, and the zone of certainty in determining risk of hypoglycemia is mapped to 0.5.

10. The method of claim 1 further comprising: using the aggregate risk of hypoglycemia to estimate the probability of a hypoglycemic event.

11. The method of claim 1, wherein aggregating the plurality of probability signals includes combining the plurality of probability signals using the Bayes formula.

12. The method of claim 1, wherein aggregating the plurality of probability signals includes the steps of:
    determining an individual's chronic risk of hypoglycemia based on self-monitored blood glucose data by the formula $$P^1_{hypo} = P_1(eChronicRisk)$$

if a probability signal is available for acute risk of hypoglycemia based on self-monitored blood glucose data is available, updating the aggregate risk of hypoglycemia by the formula $$P^2_{hypo} = \frac{P^1_{hypo} \cdot P_2(eAcuteRisk)}{P^1_{hypo} \cdot P_2(eAcuteRisk) + (1 - P^1_{hypo}) \cdot (1 - P_2(eAcuteRisk))}$$

and, for each additional probability signal, updating the aggregate risk of hypoglycemia by the formula $$P^3_{hypo} = \frac{P^2_{hypo} \cdot P_3(\text{Exercise})}{P^2_{hypo} \cdot P_3(\text{Exercise}) + (1 - P^2_{hypo}) \cdot (1 - P_3(\text{Exercise}))},$$

where "Exercise" indicates one of the data sources of the additional probability signal.

13. The method of claim 1 further comprising: displaying an alert on a display of a portable computing device based on the determined aggregated risk of hypoglycemia.

14. The method of claim 1 further comprising: communicating an instruction to an insulin pump based on the determined aggregated risk of hypoglycemia.

15. A system for tracking hypoglycemia risk comprising:
    a digital processor;
    a memory in communication with the digital processor, wherein the memory contains instructions configured to be executed by the processor to
    determine, for each of a plurality of intermittently available data sources, one or more probability signals for impending hypoglycemia, wherein each probability signal for an available data source is based on one or more inputs therefrom and each probability signal for an unavailable data source is based on a lack of input therefrom and assigned a probability value corresponding to a zone of uncertainty of risk of hypoglycemia; and
    determine an aggregate risk of hypoglycemia based on the plurality of intermittently available data sources by aggregating the plurality of probability signals;
    wherein at least one data source of the plurality of intermittently available data sources comprises continuous glucose monitoring (CGM) data.

16. The system of claim 15 further comprising:
    a display; and
    wherein the digital processor is configured to generate an alert on the display if the determined aggregate risk of hypoglycemia indicates a probability of a hypoglycemic event exceeds a predetermined threshold.

17. The system of claim 15 further comprising:
a continuous blood glucose monitoring sensor in communication with the digital processor, the continuous blood glucose monitoring sensor configured to generate said continuous glucose monitoring data and communicate said data to the digital processor.

18. The system of claim 15 further comprising:
an insulin pump in communication with the digital processor and configured to dispense or not dispense insulin in response to the determined aggregate risk of hypoglycemia.

19. The system of claim 15 further comprising:
an insulin pump in communication with an automatic insulin delivery (AID) algorithm programmed to attenuate or discontinue insulin delivery in response to the determined aggregate risk of hypoglycemia.

* * * * *